United States Patent
Blair et al.

(10) Patent No.: US 9,764,157 B2
(45) Date of Patent: Sep. 19, 2017

(54) METHODS, SYSTEMS, AND APPARATUS FOR REDUCING THE FREQUENCY AND/OR SEVERITY OF PHOTOPHOBIC RESPONSES OR FOR MODULATING CIRCADIAN CYCLES

(71) Applicant: University of Utah Research Foundation, Salt Lake City, UT (US)

(72) Inventors: Steven M. Blair, Salt Lake City, MI (US); Bradley Jay Katz, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 153 days.

(21) Appl. No.: 14/338,182

(22) Filed: Jul. 22, 2014

(65) Prior Publication Data

US 2014/0327967 A1 Nov. 6, 2014

Related U.S. Application Data

(63) Continuation-in-part of application No. 14/160,374, filed on Jan. 21, 2014, which is a continuation-in-part (Continued)

(51) Int. Cl.
*A61N 5/06* (2006.01)
*G02B 5/28* (2006.01)
(Continued)

(52) U.S. Cl.
CPC .......... *A61N 5/0618* (2013.01); *A61M 21/02* (2013.01); *G02B 5/22* (2013.01); *G02B 5/285* (2013.01);
(Continued)

(58) Field of Classification Search
CPC .......... A61N 5/0618; A61N 2005/0667; G02B 5/22; G02B 5/285; G02B 5/289;
(Continued)

(56) References Cited

U.S. PATENT DOCUMENTS 4,527,183 A 7/1985 Anthony
5,218,386 A 6/1993 Levien
(Continued)

FOREIGN PATENT DOCUMENTS

DE 102005044031 3/2007
DE 102007007777 6/2008
(Continued)

OTHER PUBLICATIONS

U.S. Appl. No. 13/979,876, Feb. 25, 2016, Office Action.
(Continued)

*Primary Examiner* — Christine H Matthews
*Assistant Examiner* — Joshua D Lannu
(74) *Attorney, Agent, or Firm* — Workman Nydegger

(57) ABSTRACT

An optical filter may reduce the frequency and/or severity of photophobic responses or for modulating circadian cycles by controlling light exposure to cells in the human eye in certain wavelengths, such as 480 nm and 590 nm, and a visual spectral response of the human eye. The optical filter may disrupt the isomerization of melanopsin in the human eye reducing the availability of the active isoform, whereas the attenuation of light weighted across the action potential spectrum of the active isoform attenuates the phototransduction cascade leading to photophobic responses. Embodiments of an optical filter are described. In one embodiment an optical filter may be configured to transmit less than a first amount of light in certain wavelengths, and to transmit more than a second amount of light weighted across the visual (Continued)

spectral response. Methods of use and methods of manufacturing optical filters are also described.

17 Claims, 17 Drawing Sheets

Related U.S. Application Data of application No. 13/979,876, filed as application No. PCT/US2012/021500 on Jan. 17, 2012.

(60) Provisional application No. 61/433,344, filed on Jan. 17, 2011.

(51) Int. Cl.
| | | |
|---|---|---|
| G02B 5/22 | (2006.01) | |
| A61M 21/02 | (2006.01) | |
| G02C 7/10 | (2006.01) | |
| A61M 21/00 | (2006.01) | |

(52) U.S. Cl.
CPC ..... *G02C 7/104* (2013.01); *A61M 2021/0044* (2013.01); *A61N 2005/0667* (2013.01); *G02B 5/289* (2013.01); *G02B 2207/101* (2013.01)

(58) Field of Classification Search
CPC ............ G02B 2207/101; A61M 21/02; A61M 2021/0044; G02C 7/104
See application file for complete search history.

(56) References Cited

U.S. PATENT DOCUMENTS

| | | | |
|---|---|---|---|
| 5,402,190 | A | 3/1995 | Waldman |
| 5,737,045 | A * | 4/1998 | Abileah ............ G02F 1/133604 349/104 |
| 5,946,114 | A * | 8/1999 | Loiseaux ............... G02B 5/203 348/E9.027 |
| 6,420,032 | B1 | 7/2002 | Iacovangelo |
| 6,610,081 | B2 | 8/2003 | Saathoff |
| 7,380,940 | B2 | 6/2008 | Anderson et al. |
| 7,438,411 | B2 | 10/2008 | Payne |
| 7,556,376 | B2 | 7/2009 | Ishak |
| 7,854,505 | B2 | 12/2010 | Cunningham |
| 7,988,318 | B1 * | 8/2011 | Smith .................. G01N 21/255 362/184 |
| 2002/0044254 | A1 | 4/2002 | Saathoff |
| 2003/0161257 | A1 | 8/2003 | Yusu |
| 2004/0085660 | A1 | 5/2004 | Hara et al. |
| 2005/0149993 | A1 | 7/2005 | Panda |
| 2005/0164169 | A1 | 7/2005 | Malak |
| 2006/0092374 | A1 | 5/2006 | Ishak |
| 2006/0158732 | A1 | 7/2006 | Ramadan |
| 2006/0189113 | A1 | 8/2006 | Vanheusden et al. |
| 2007/0298242 | A1 * | 12/2007 | Huo ........................ G02C 5/00 428/328 |
| 2008/0065177 | A1 | 3/2008 | Casper |
| 2008/0221674 | A1 | 9/2008 | Blum et al. |
| 2009/0022995 | A1 | 1/2009 | Graham et al. |
| 2010/0149483 | A1 | 6/2010 | Chiavetta, III |
| 2010/0246009 | A1 | 9/2010 | Polley |
| 2010/0328763 | A1 | 12/2010 | Seo et al. |
| 2011/0060062 | A1 | 3/2011 | Wang et al. |
| 2011/0075263 | A1 | 3/2011 | Liberman |
| 2011/0223255 | A1 | 9/2011 | Thiesen et al. |
| 2013/0062637 | A1 | 3/2013 | Reed et al. |
| 2013/0100443 | A1 | 4/2013 | Li et al. |
| 2013/0130018 | A1 | 5/2013 | Poncelet et al. |
| 2013/0258456 | A1 | 10/2013 | Hashimura |
| 2014/0160569 | A1 | 6/2014 | Blair et al. |
| 2015/0138661 | A1 | 5/2015 | Blair et al. |
| 2015/0168616 | A1 | 6/2015 | Blair et al. |

FOREIGN PATENT DOCUMENTS

| | | |
|---|---|---|
| DE | 102011050870 | 12/2012 |
| JP | 2007199421 | 8/2007 |
| WO | 2004021071 | 3/2004 |
| WO | 2004077453 | 9/2004 |
| WO | 2006097794 | 9/2006 |
| WO | 2007011331 | 1/2007 |
| WO | 2007133197 | 11/2007 |
| WO | 2010111499 | 9/2010 |
| WO | 2012154535 | 11/2012 |
| WO | 2012177296 | 12/2012 |
| WO | 2014011581 | 1/2014 |
| WO | 2015073933 | 5/2015 |
| WO | 2016014713 | 1/2016 |

OTHER PUBLICATIONS

U.S. Appl. No. 14/160,374, Apr. 7, 2016, Office Action.
U.S. Appl. No. 14/160,374, filed Jan. 21, 2014, Blair.
U.S. Appl. No. 13/979,876, filed Feb. 24, 2014, Blair.
International Search Report and Written Opinion PCT/US2012/021500 Dated May 8, 2012.
Balzers et al., "Design of Optical Minus Filters," Journal of the Optical Society of America, vol. 61, No. 3, (1971).
Berson et al., "Phototransduction by Retinal Ganglion Cells That Set the Circadian Clock," Science, 295 (2002).
Blackburn "FL-41 Tint Improves Blink Frequency, Light Sensitivity, and Functional Limitations in Patients with Benign Essential Blepharospasm," Ophthalmology 2009 116(5) 997-1001.
Bogoslovov et al. Effect of Silica Nanoparticles on the Local Segmental Dynamics in Poly(vinyl acetate), Macromolecules, 2008, vol. 41, pp. 1289-1296.
Czeisler "Sleep and Circadian Rhythms in Humans," Cold Spring Harbor Symposia on Quantitative Biology, 2007, 72:579-97.
Czeisler, "The Effect of Light on the Human Circadian Pacemaker," CIBA Foundation Symposium. 1995: 183:254-90.
Duffy et al. "Entertainment of the Human Circadian System by Light." Journal of Biological Rhythms, 2005 20(4): 326-38.
European Search Report for EP15151981 dated May 19, 2015.
Good et al. "The Use of Tinted Glasses in Childhood Migraine Headache," Headache: The Journal of Head and Face Pain, 1991 31:8 533-6.
Hannibal et al. "Roles of PACAP-Containing Retinal Ganglion Cells in Circadian Timing," International Review of Cytology, 2006, vol. 251, pp. 1-39.
International Search Report for PCT/US2014/65848 dated Mar. 5, 2015.
Khlebtsov et al. "The Effect of the Size, Shape, and Structure of Metal Nanoparticles on the Dependence of Their Optical Properties on the Refractive Index ofa Disperse Medium," Optics and Spectroscopy, vol. 98, No. 1, 2005, pp. 77-83.
Larouche et al., "OpenFilters: Open-Source Software for the Design, Optimization, and Synthesis of Optical Filters," Applied Optics, vol. 47, No. 13, (2008).
Mure et al "Melanopsin Bistability: A Fly's Eye Technology in the Human Retina," PLoS One. 2009 4(6):e5991.
Noseda et al. "A Neural Mechanism for Exacerbation of Headache by Light" Nature Neruoscience, 2010 13:2 239-45.
Sahoo et al. "Residual Polyvinyl Alcohol Associated with Poly (D,L-lactide-co-glycolilde) Nanoparticles Affects Their Physical Properties and Cellular Uptake," Journal of Controlled Release, vol. 82, 2002, pp. 105-114.
Satchidananda Panda et al., "Illumination of the Melanopsin Signaling Pathway," Science, 307 (2005).
Wang et al., "Theory and Applications of Guided-Mode Resonance Filters," Applied Optics, vol. 32, No. 14, (1993).
Willets et al. "Localized Surface Plasmon Resonance Spectroscopy and Sensing," Annual Review in Physical Chemistry, vol. 58, 2007, pp. 267-297.
International Search Report and Written Opinion for PCT/US2015/041610 dated Oct. 2, 2015.
European Search Report for EP12802027 dated Nov. 30, 2015.

(56) References Cited

OTHER PUBLICATIONS

Hoggan et al., "Thin Film Optical Notch Filter Spectacle Coatings for the Treatment of Migraine and Photophobia," In Press. Journal of Clinical Neuroscience, 2016.
Kojima et al., "UV-Sensitive Photoreceptor Protein OPN5 in Humans and Mice," PLoS One 6(10): e26388. doi: 10.1371/journal.pone.0026388.
U.S. Appl. No. 14/542,564, Nov. 2, 2016, Restriction Requirement.
U.S. Appl. No. 14/542,478, Nov. 3, 2016, Office Action.
U.S. Appl. No. 13/979,876, Nov. 18, 2016, Notice of Allowance.
U.S. Appl. No. 14/160,374, Oct. 20, 2016, Office Action.
U.S. Appl. No. 14/160,374, May 8, 2017, Notice of Allowance.
European Search Report for application No. 14861298.9 dated Jun. 2, 2017.
U.S. Appl. No. 14/542,564, Jun. 5, 2017, Office Action.
U.S. Appl. No. 14/542,478, Jun. 2, 2017, Final Office Action.

\* cited by examiner

METHODS, SYSTEMS, AND APPARATUS FOR REDUCING THE FREQUENCY AND/OR SEVERITY OF PHOTOPHOBIC RESPONSES OR FOR MODULATING CIRCADIAN CYCLES

CROSS-REFERENCE TO RELATED APPLICATIONS

The present application is a continuation-in-part of: U.S. patent application Ser. No. 14/160,374, filed Jan. 21, 2014, entitled "METHODS, SYSTEMS, AND APPARATUS FOR REDUCING THE FREQUENCY AND/OR SEVERITY OF PHOTOPHOBIC RESPONSES OR FOR MODULATING CIRCADIAN CYCLES"; which claims the benefit and priority of: U.S. patent application Ser. No. 13/979,876, filed Jul. 16, 2013, entitled "APPARATUS AND METHODS FOR REDUCING FREQUENCY OR SEVERITY TO PHOTOPHOBIC RESPONSES OR MODULATING CIRCADIAN CYCLES"; which claims the benefit and priority of: PCT Patent Application Ser. No. PCT/US2012/021500, filed Jan. 17, 2012, entitled "APPARATUS AND METHODS FOR REDUCING FREQUENCY OR SEVERITY TO PHOTOPHOBIC RESPONSES OR MODULATING CIRCADIAN CYCLES"; which claims the benefit of and priority to U.S. Provisional Patent Application Ser. No. 61/433,344, filed Jan. 17, 2011, entitled "METHODS, SYSTEMS, AND APPARATUS FOR REDUCING THE FREQUENCY AND/OR SEVERITY OF PHOTOPHOBIC RESPONSES OR FOR MODULATING CIRCADIAN CYCLES", the disclosures of which are each incorporated herein by reference in their entireties.

BACKGROUND OF THE DISCLOSURE

1. The Field of the Invention

Photophobia, or light sensitivity, describes an adverse response to light that characterizes several neurologic conditions. The present invention relates to managing the effects of light on a subject. More particularly, the present invention relates to methods, systems, and apparatus for reducing the frequency and/or severity of photophobic responses or for modulating circadian cycles.

2. The Relevant Technology

The retina of the eye contains various photoreceptor cells. These photoreceptor cells include rods (which are involved in black-and-white and low light vision), cones (which are involved in daytime vision and color perception), and melanopsin ganglion cells.

The melanopsin ganglion cells are photosensitive. This photosensitivity can transmit pain through the pain pathways of the brain. These pathways are further described by Noseda et al. in A Neural Mechanism for Exacerbation of Headache by Light Nat Neurosci. 2010 February; 13(2):239-45 PMID 20062053, which is hereby incorporated by reference in its entirety. It has been demonstrated previously that modulating ambient light through the use of spectacle tints can be effective in the treatment of light-sensitive neurological conditions including migraine and benign essential blepharospasm. A description of these beneficial effects may be found in Good et al. The Use of Tinted Glasses in Childhood Migraine Headache. 1991 September; 31(8):533-6 PMID 1960058 and Blackburn et al. FL-41 Tint Improves Blink Frequency Light Sensitivity and Functional Limitations in Patients with Benign Essential Blepharospasm Ophthalmology. 2009 May; 116(5):997-1001 PMID 19410958, which are both hereby incorporated by reference in their entirety In addition to pain pathways, melanopsin ganglion cells also connect to the suprachiasmatic nucleus, where they participate in entrainment of circadian rhythms. These connections are further described by Hannibal J. Roles of PACAP-containing retinal ganglion cells in circadian timing. Int Rev Cytol. 2006; 251:1-39. Review. PubMed PMID: 16939776, which is hereby incorporated by reference in its entirety.

All animals have an intrinsic "clock" that synchronizes them with the earth's light/dark cycle of 24 hours. This clock establishes an internal rhythm of about ("circa") one day ("dian"). This phenomenon is described by Czeisler C A, Gooley J J. Sleep and circadian rhythms in humans. Cold Spring Harb Symp Quant Biol. 2007; 72:579-97. Review. PubMed PMID: 18419318, which is hereby incorporated by reference in its entirety. However, in order to stay optimally synchronized with the dark/light cycle, the body's internal clock must be reset each day. This entrainment occurs when light in the environment is absorbed by the melanopsin ganglion cells and a signal is transmitted to that part of the brain that serves as the body's "master clock", the suprachiasmatic nucleus, as described in Czeisler C A. The effect of light on the human circadian pacemaker. Ciba Found Symp. 1995; 183:254-90; discussion 290-302. Review. PubMed PMID: 7656689 and Duffy J F, Wright K P Jr. Entrainment of the human circadian system by light. J Biol Rhythms. 2005 August; 20(4):326-38. Review. PubMed PMID: 16077152, both of which are hereby incorporated by reference in their entireties.

Rhodopsin is the photosensitive molecule in the rods and cones of the eye. Rhodopsin has two metastable isomers including an active and an inactive state. When exposed to light, the rhodopsin isomerizes to an inactive isoform. The inactive isoform of rhodopsin can be recycled in the retinoid cycle. During the retinoid cycle, the rhodopsin leaves the photoreceptor and enters the retinal pigment epithelium. After being recycled to an active isoform, the rhodopsin returns to the photoreceptor. The melanopsin of the melanopsin ganglion cells is believed to undergo a similar process as described in Mure L S, Cornut P L, Rieux C, Drouyer E, Denis P, Gronfier C, Cooper H M. Melanopsin bistability: a fly's eye technology in the human retina. PLoS One. 2009 Jun. 24; 4(6):e5991. PubMed PMID: 19551136, which is incorporated hereby by reference in its entirety.

Therefore, it would be desirable to manage the effects of light on a subject. More particularly, it would be desirable to provide methods, systems, and apparatus for reducing the frequency and/or severity of photophobic responses. It would be also desirable to provide methods, systems, and apparatus for modulating circadian cycles.

BRIEF SUMMARY

As the melanopsin ganglion cells are sensitive to light wavelengths near 480 nm and are associated with pain pathways in humans, managing the painful effects caused by certain types of light would be desirable. For example, stimulation of the melanopsin ganglion cells may affect the frequency and/or severity of photophobic responses, so it may be beneficial in some circumstances to reduce the direct light stimulation of these cells, or in other circumstances to reduce the amount of exposure to light not directly associated with the stimulation of these cells. These photophobic responses include migraine headache, light sensitivity associated with a concussion or traumatic brain injury, light sensitive epilepsy, and light sensitivity associated with benign essential blepharospasm. The melanopsin ganglion cells are also associated with circadian cycles. Thus, methods, systems, and apparatus for reducing the frequency and/or severity of photophobic responses and/or for modulating circadian cycles by controlling light exposure to melanopsin ganglion cells or other portions of the eye are provided.

An embodiment of an apparatus for reducing the frequency and/or severity of photophobic responses or for modulating circadian cycles is described. The apparatus includes an optical filter configured to transmit less than a first amount of light weighted across the absorption spectrum of the bistable isoforms of melanopsin, and to transmit more than a second amount of light weighted across the visual spectral response. As examples, the light spectrum associated with the absorption spectrum of the active isoform of melanopsin is near 480 nm wavelength, and a light spectrum associated with the absorption spectrum of the inactive isoform of melanopsin is near 590 nm wavelength.

In some embodiments, the first amount of light is about 50% of the light weighted across the absorption spectrum of one or both of the bistable isoforms of melanopsin and the second amount of light is about 75% or greater of the light weighted across the visual spectral response. The first amount of light, in other embodiments, is about 25% of the light weighted across the absorption spectrum of one or both of the bistable isoforms of melanopsin and the second amount of light is about 60% or greater of the light weighted across the visual spectral response. In further embodiments, the first amount of light is approximately all of the light weighted across the absorption spectrum of one or both of the bistable isoforms of melanopsin. The second amount of light, in still further embodiments, is approximately all of the light outside of the absorption spectrum of one or both of the bistable isoforms of melanopsin and/or weighted across a spectrum that lies outside the absorption spectrum of one or both of the bistable isoforms of melanopsin, weighted across the visual response spectrum. In yet further embodiments, a ratio of the attenuation of the first amount of the light weighted across the absorption spectrum of one or both of the bistable isoforms of melanopsin to the attenuation of the second amount of the light weighted across the visual spectral response is more than one.

The first amount of light, in some embodiments, is substantially all light below a long pass filter wavelength within the action potential spectrum of the melanopsin ganglion cells and the second amount of light is all light across the visual spectral response with a wavelength above the long pass filter wavelength. In further embodiments, the first amount of light is substantially all light above a short pass filter wavelength near 590 nm and the second amount of light may be substantially all light across the visual spectral response with a wavelength below the short pass filter wavelength.

In some embodiments, the second amount of light includes a third amount of light having a wavelength that is less than a maximum relative response of the action potential spectrum of the melanopsin ganglion cells and/or greater than about 590 nm. The second amount of light, in other embodiments, includes a third amount of light having a wavelength that is greater than a maximum relative response of the absorption spectrum of one or both of the bistable isoforms of melanopsin. In further embodiments, the second amount of light includes a third amount of light having a wavelength that is lower than a maximum relative response of the absorption spectrum of one or both of the bistable isoforms of melanopsin and a fourth amount of light that is greater than the maximum relative response of the absorption spectrum of one or both of the bistable isoforms of melanopsin.

In some embodiments, the first amount of light is a dose of light (i.e. across the absorption spectrum of one or both of the bistable isoforms of melanopsin) experienced by a cell in the eye—retinal ganglion cells or other cells of a subject ($D_{rec}$)—and the second amount of light is a dose of light experienced over the visual response spectrum ($D_{vis}$), and wherein a ratio including the first amount of light and the second amount of light is defined as a figure of merit (FOM), the figure of merit being determined by:

$$FOM = \frac{1 - \frac{D_{rec}}{D_{rec}(T=1)}}{1 - \frac{D_{vis}}{D_{vis}(T=1)}}$$

where $D_{rec}$ (T=1) is the first amount of light in the absence of an optical filter, and $D_{vis}$ (T=1) is the second amount of light in the absence of an optical filter. The figure of merit of the optical filter, in some embodiments, may include about one, more than about one, more than about 1.3, more than about 1.5, more than about 1.8, more than about 2.75, more than about 3, more than about 3.3. Other figures of merit may be used in other embodiments.

In some embodiments, the first amount of light defines a spectral width that has a median at a median of the absorption spectrum of one or both of the bistable isoforms of melanopsin. The first amount of light and the second amount of light, in further embodiments, are determined based on the characteristics of ambient light. In still further embodiments, the first amount of light and the second amount of light are selectively adjustable by way of a transition, -photochromic, or electrochromic type dye, pigment or coating.

The optical filter, in some embodiments, includes at least one layer configured to minimize or reduce the effect of an angle of incidence of the received light. In further embodiments, the optical filter further comprises a substrate that includes a tint by impregnation or by coating.

An embodiment of a system for reducing the frequency and/or severity of photophobic responses or for modulating circadian cycles is described. The system includes a substrate, a first layer disposed on the substrate, and a second layer disposed adjacent the first layer. The first layer includes a high index material. The second layer includes a low index material.

In further embodiments, the system may include additional layers and/or types of material, wherein the materials cooperate to transmit less than a first amount of light weighted across the action potential spectrum of the melanopsin ganglion cells and to transmit more than a second amount of light weighted across the visual spectral response. In some embodiments, increasing the number of layers in the optical filter increases transmission of light outside the action potential spectrum.

An embodiment of a method of manufacturing an optical filter for reducing the frequency and/or severity of photophobic responses is described. The method includes determining an appropriate light spectrum. A first light dose to be experienced by one or both of the bistable isoforms of melanopsin in the subject is determined. A second light dose associated with the visual response spectrum is determined. An optical filter is manufactured using the first light dose and the second light dose.

In some embodiments, an action potential spectrum of an individual's melanopsin ganglion cells is determined. The optical filter, in further embodiments, is configured to attenuate the first amount of light based on the individual's melanopsin ganglion cells. In still further embodiments, the optical filter is manufactured based on visual response spectrum characteristics.

The optical filter, in some embodiments, is a notch filter. In further embodiments, the notch filter is configured to block light that strikes at a non-normal incidence angle. The notch filter, in still further embodiments, includes a filter optimized for a plurality of tilted incidence angles. In yet further embodiments, the notch filter is designed with a slight red shift. The notch filter, in even further embodiments, includes a filter notch that attenuates light across a spectral width.

In some embodiments, manufacturing of the optical filter includes using dielectric multi-layers, embedded nanoparticle coatings, a color filter, tint, resonant guided-mode filter, a rugate filter, and any combination thereof. The embedded nanoparticle coatings, in further embodiments, include at least one of metallic nanoparticles, dielectric nanoparticles, semiconductor nanoparticles, quantum dots, magnetic nanoparticles, or core-shell particles having a core material in a core and a shell material serving as a shell. In still further embodiments, the at least metallic nanoparticles include at least one of Al, Ag, Au, Cu, Ni, Pt, or other metallic nanoparticles, wherein the dielectric nanoparticles include at least one of $TiO_2$, $Ta_2O_5$, or other dielectric nanoparticles. The semiconductor nanoparticles or quantum dots, in yet further embodiments, include at least one of Si, GaAs, GaN, CdSe, CdS, or other semiconductor nanoparticles. In even further embodiments, a shape of the embedded nanoparticles in the embedded nanoparticle coatings is spherical, elliptical, or otherwise shaped. In some embodiments, an extinction spectrum of the embedded nanoparticles is determined using Mie scattering theory.

An embodiment of a method for reducing the frequency and/or severity of photophobic responses or for modulating circadian cycles is described. The method includes receiving an amount of light. Less than a first amount of the light weighted across the absorption spectrum of one or both of the bistable isoforms of melanopsin is transmitted. More than a second amount of the light weighted across the visual spectral response is transmitted. The attenuation of light weighted across the absorption spectrum of one or both of the bistable isoforms of melanopsin disrupts the isomerization of one or both of the bistable isoforms of melanopsin.

BRIEF DESCRIPTION OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

DETAILED DESCRIPTION

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

The present invention relates to managing the effects of light on a subject. Some applications of the present invention relate to methods, systems, and apparatus for reducing the frequency and/or severity of photophobic responses or for modulating circadian cycles.

Different individuals experience photophobic responses in different ways. The wavelengths and, therefore, pathways that trigger adverse reactions to light can vary depending on the patient. However, there are some common wavelengths that are more commonly associated with photophobic responses than others. For example, the melanopsin ganglion cells in the eye are sensitive to light at a wavelength of about 480 nm. In some individuals, this may be linked to those individual's light-sensitive neurological conditions. Controlling exposure to light near the 480 nm wavelength may yield benefits to those individuals and reduce or prevent their light-sensitive neurological conditions. Alternatively or in addition, regulating exposure to that same light may also assist in controlling an individual's circadian rhythms. In the same or other individuals, regulating the exposure of the eye to light near a 620 nm wavelength or other wavelengths may also yield benefits in reducing or preventing light-sensitive neurological conditions or managing an individual's circadian rhythms. While the following example refers to the attenuation of light having wavelengths near 480 nm and the exposure of melanopsin ganglion cells to the same light near 480 nm, it may be understood that a similar filter and methods may be used to attenuate light at other wavelengths and received by other cells in the eye. For example, a similar filter and method may be used to attenuate light at or about 620 nm. In another example, a similar filter and method may be used to attenuate light at or about 590 nm.

Figure 1:
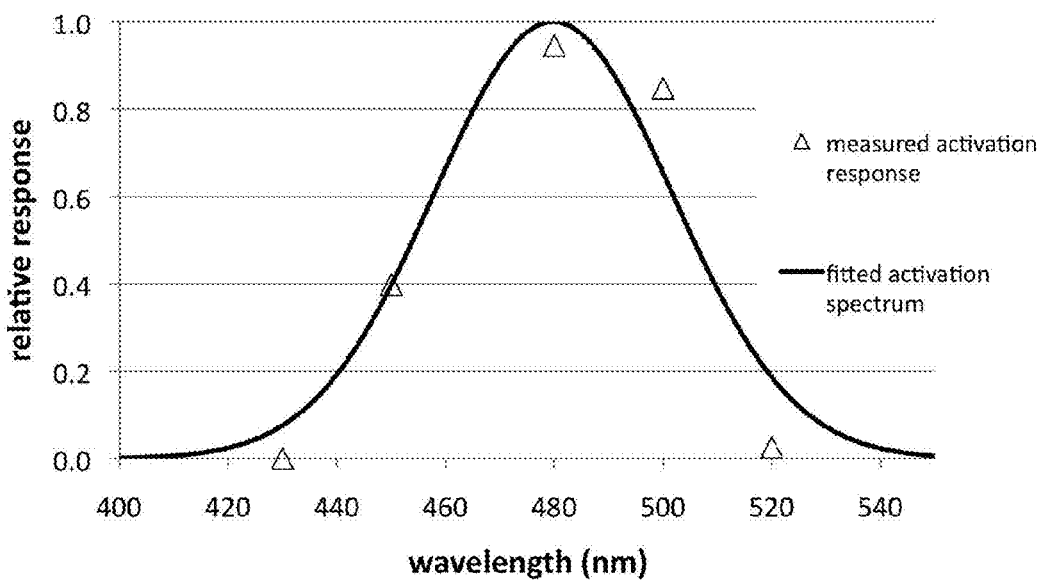
FIG. 1 illustrates an exemplary measured action potential spectrum for melanopsin cells, which is normalized to unity magnitude, with a Gaussian fit to the measured data points.

Because the melanopsin ganglion cells have been implicated in photophobia and in the onset of migraines in a number of photophobic subjects, it is desirable to block at least portions of that part of the visible spectrum that activates these cells. Photophobia is associated with light-sensitive neurological conditions, including migraine headaches, benign essential blepharospasm and traumatic brain injury (TBI). FIG. 1 illustrates an example of the measured action potential spectrum for melanopsin cells, which is normalized to unity magnitude, and a Gaussian fit to the measured data points. This Gaussian fit may be used in at least one embodiment of a filter design, but this should not be interpreted as the spectral basis for optimal filters, as more refined measurements of the action potential spectrum may become available. These refined measurements may motivate additional filter designs or methods following the process described here, or via similar processes. Optimizations of the methods, systems, and apparatus described herein based on more refined measurements of the action potential spectrum are contemplated.

In some embodiments, light may be blocked (i.e. attenuated) over a certain wavelength range appropriate for photophobia prevention, while minimizing the distortion of the visible spectrum. In other embodiments, the methods, systems, and apparatus described in this application may also be used to manipulate the body's circadian system.

Embodiments of optical filters are described that block a certain part of the optical spectrum that is suspected to trigger and/or exacerbate these photophobic responses. These filters can be applied to eyewear (such as spectacles, goggles, clip-ons, or other eyewear), lenses (including contact lenses), computer screens, windows, car windshields, lighting substrates, light bulbs (incandescent, fluorescent, CFL, LED, gas vapor, etc.), or any other optical element. These optical filters may be applied to crown glasses (including BK7), flint glasses (including $BaF_8$), $SiO_2$, plastics (such as polycarbonate, CR-39, and trivex), other substrates, and combinations thereof.

Although the majority of the description focuses on photophobia prevention, the systems, methods, and apparatus described herein are also applicable to modulating circadian rhythm. For example, these filters could be used for manipulation of the body's circadian system by business people, athletes, others who travel between different time zones, or those who desire to manipulate the body's circadian system. In one example, a subject would wear at least one of the filters described herein to help them adapt to the light/dark cycle of the locale to which they are traveling. In another example at least one of the filters described herein could also be used to limit excitation of the melanopsin ganglion cells in patients with sleep disorders. In this use, a subject could wear these filters to limit their exposure to artificial light in the evening, and prevent their internal clocks from thinking that it is time to stay awake. In addition, subjects may increase exposure to light before sunrise to adjust their light/dark cycle.

Furthermore, it has also been recently clinically demonstrated that wavelengths near 620 nm also contribute to photophobic effects in certain individuals. While the precise pathways for the neurological effects are not currently fully understood, benefits may be achieved by preferentially attenuating light with wavelengths near 620 nm, as well.

Melanopsin has bistable isoforms that each exhibit unique absorption spectra. The isoforms may be an active isoform and an inactive isoform. The active isoform may be physiologically active. The inactive isoform may be physiologically inactive. Absorption of light in accordance with each isoform's absorption spectrum may lead to the isomerization of the melanopsin. Benefits may be achieved by disrupting, limiting, or preventing the isomerization of melanopsin by attenuating light at or about 590 nm.

The FL-41 lens tint is sometimes prescribed for migraine patients. The FL-41 tint blocks (via absorption) a broad range of wavelengths. These wavelengths include wavelengths associated with melanopsin absorption. The FL-41 dye can be infiltrated into certain types of plastic spectacle lenses. The amount of dye infiltrated generally determines the amount of light intensity blocked. The "FL-41 35" tinting is effective for a number of patients in indoor environments. However, if the light source increases in intensity, by for example moving to an outdoor environment, the "FL-41 35" may not be as effective.

Figure 2:
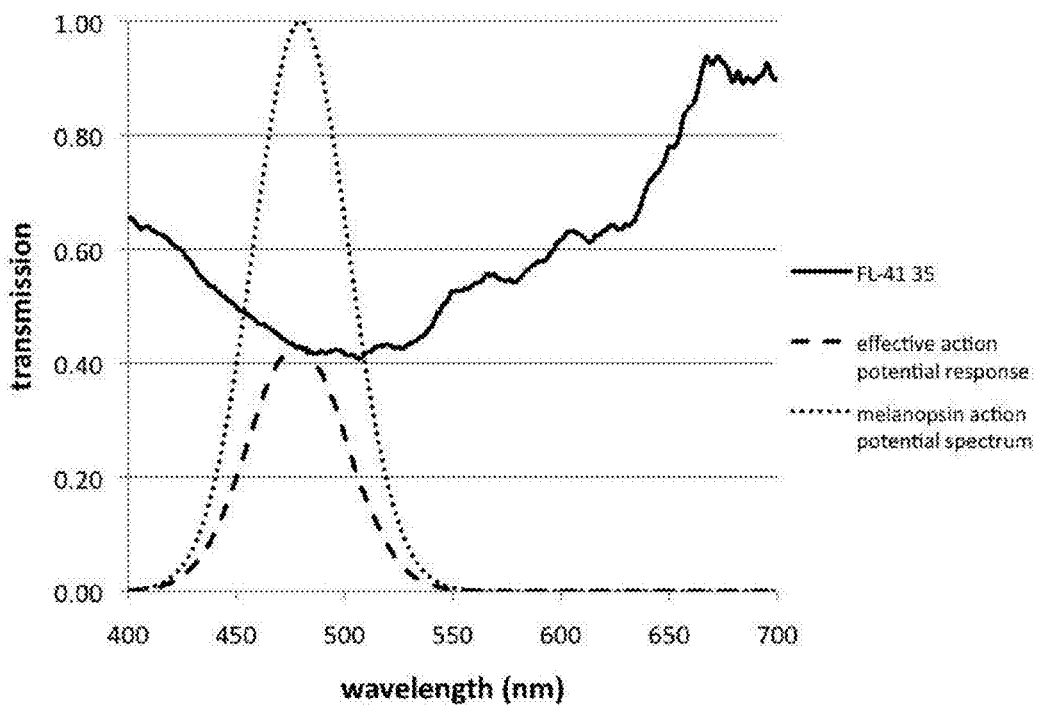
FIG. 2 illustrates the measured transmission spectrum of an exemplary "FL-41 35" filter across the "effective action potential spectrum" of melanopsin.
Figure 3:
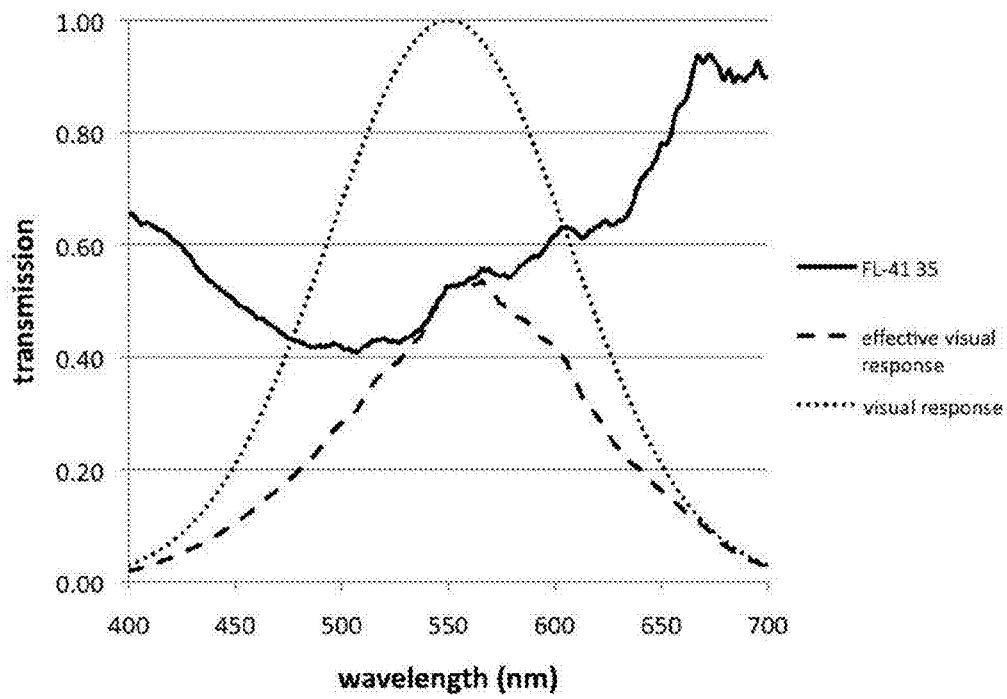
FIG. 3 illustrates the measured transmission spectrum of an exemplary "FL-41 35" filter across the visible light spectrum.

FIG. 2 shows the measured transmission spectrum of "FL-41 35". FIG. 2 also illustrates the effect of the "FL-41 35" filter on the action potential spectrum of melanopsin, a so-called "effective action potential spectrum." The "FL-41 35" tinting blocks, or attenuates, about 55% of the light that would otherwise be absorbed by the melanopsin ganglion cells. The FL-41 tinting further blocks a significant portion of the visible spectrum that is not associated with melanopsin, as shown in FIG. 3, with about a 47% attenuation across the visual response spectrum. The additional blocking the visible response spectrum may be disadvantageous. For example, blocking the visible response spectrum may adversely affect normal vision. In another example, blocking the visible response spectrum may produce a false coloration that may be distractive or otherwise less desirable for the wearer.

Figure 4:
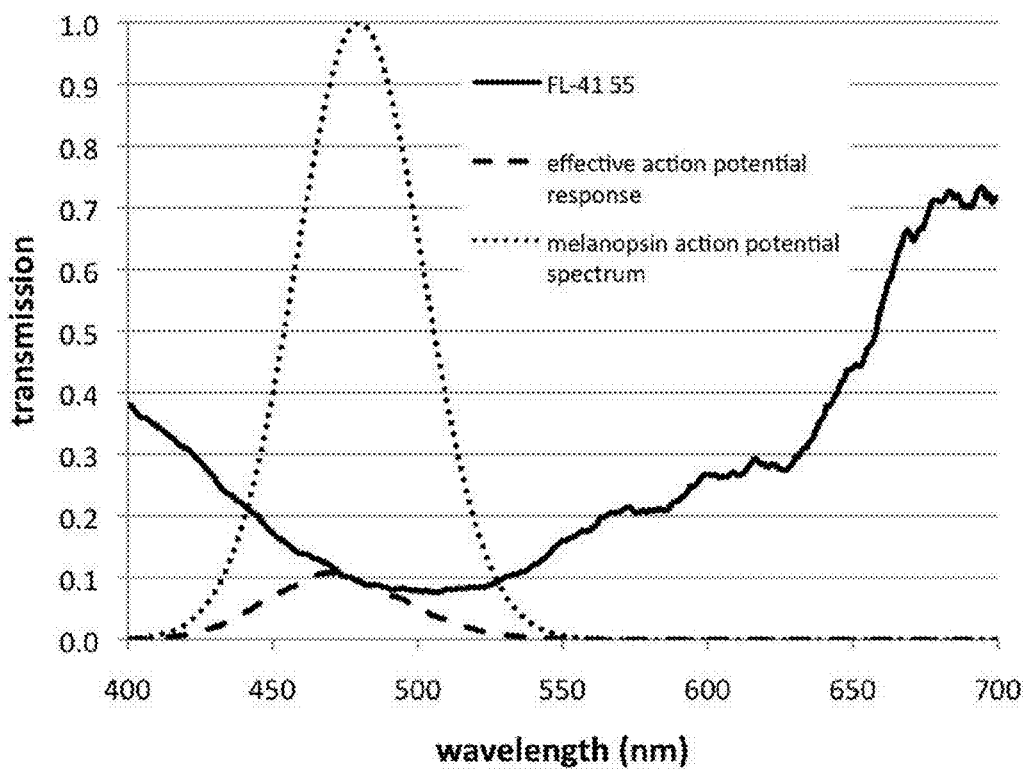
FIG. 4 illustrates the measured transmission spectrum of an exemplary "FL-41 55" filter across the "effective action potential spectrum" of melanopsin.
Figure 5:
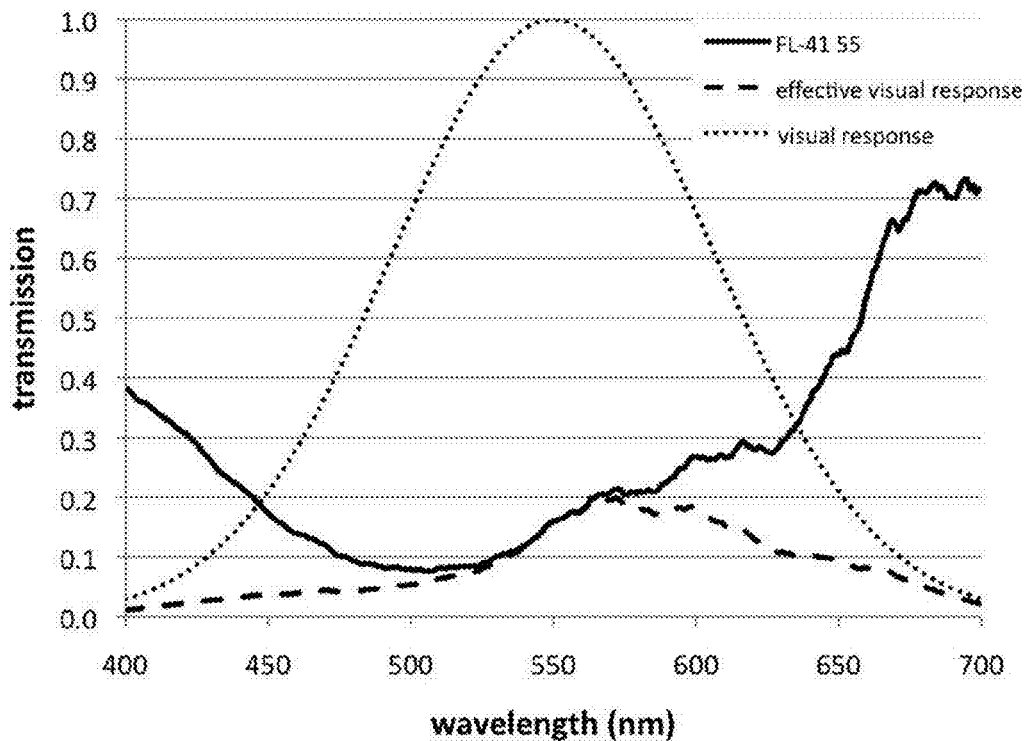
FIG. 5 illustrates the measured transmission spectrum of an exemplary "FL-41 55" filter across the visible light spectrum.

For bright light situations, such as outdoor environments, a tinting with greater level of spectral attenuation may be used, such as "FL-41 55." The transmission spectrum of this filter, along with its effect on the action potential spectrum, is shown in FIG. 4 (across the "effective action potential spectrum" of melanopsin) and 5 (across the visible light spectrum). This filter attenuates about 89% of the light that would otherwise be absorbed by melanopsin cells, but also attenuates about 81% of the visual response spectrum. This additional spectral attenuation can also impair vision in low light levels or other situations.

Overall, the general drawbacks to FL-41 include: a rose colored appearance, distorted color perception; limited applicability (i.e. it may only be applied to certain plastics and may not be applied to glass lenses, computer screens, windows, car windshields, lighting substrates, light bulbs, or other optical elements); and poor quality control over the tinting process (due in part to variations in the tintable hard coating layers). Although FL-41 may be effective in certain applications, it is not designed to down-regulate the stimulation of the melanopsin ganglion cells and their connections to pain centers in the brain. For these reasons, it may be desirable to develop other embodiments of filters.

One example of a more desirable optical filter for the treatment of light sensitive conditions may include a long-pass filter. To regulate exposure of the melanopsin ganglion cells to wavelengths of about 480 nm, a long pass filter may highly transmit wavelengths longer than about 500 nm or 520 nm, while attenuating light at wavelengths shorter than about 500 nm or 520 nm. Similarly, to regulate exposure of cells in the human eye to wavelengths of about 620 nm, a short pass filter may highly transmit wavelengths shorter than 600 nm or about 580 nm, while attenuating light at wavelengths longer than about 600 nm or about 580 nm.

Other examples of more desirable optical filters may include filters that only block the spectrum of light absorbed by melanopsin or other specific wavelengths, while generally transmitting the rest of the light spectrum, with the spectral transmission response of the filter taking the form of a notch, sometimes called a band stop or minus filter. In the case of melanopsin the center position of the notch may be near the absorption maximum of the melanopsin pathway (about 480 nm), but other positions may be effective. The spectral width of the notch may approximately match the width of the action potential spectrum, which is about 50 to 60 nm, although other widths are contemplated.

Figure 6:
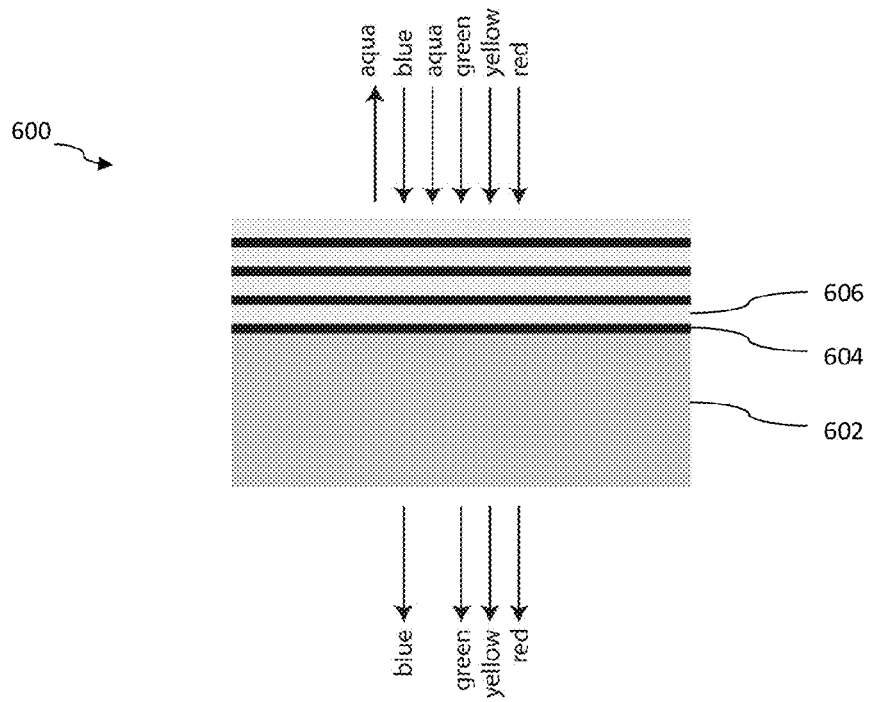
FIG. 6 is an example of a filter using multi-layer dielectric thin films of distinct refractive indices.
Figure 7:
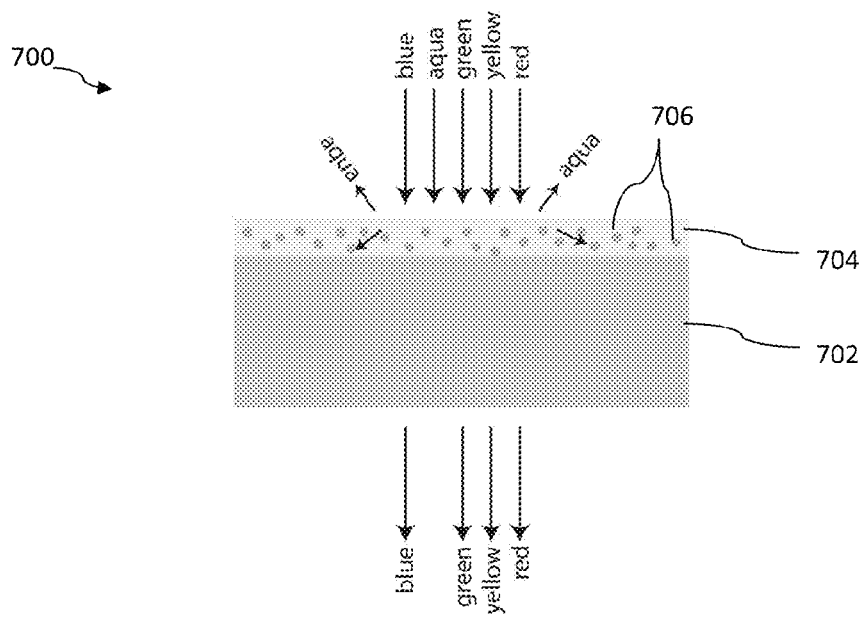
FIG. 7 is an example of a filter using an embedded nanoparticle coating designed to scatter light in the aqua region of the visible light spectrum.

Optical filter technologies such as tints comprised of dye mixtures, dielectric multi-layers (an example of which is shown in FIG. 6), and embedded nanoparticle coatings (an example of which is shown in FIG. 7), other filter technologies such as resonant waveguide filters, or combinations thereof may be used to create a filter according to the present disclosure. Nanoparticle coatings that may be used for optical filters according to the present disclosure may include metallic nanoparticles (e.g. Al, Ag, Au, Cu, Ni, Pt), dielectric nanoparticles (e.g. $TiO_2$, $Ta_2O_5$, etc.), semiconductor nanoparticles or quantum dots (e.g. Si, GaAs, GaN, CdSe, CdS, etc.), magnetic nanoparticles, core-shell particles consisting of one material in the core and another serving as a shell, other nanoparticles, or combinations thereof. Shapes of these particles may be spherical, ellipsoidal, otherwise shaped, or combinations thereof. Host materials may include polymers, sol-gels, other host materials, or combinations thereof. The extinction spectrum of these nanoparticles can be calculated using Mie scattering theory or variations thereof.

An embodiment of a multi-layer filter 600, shown in FIG. 6, includes a substrate 602, a first layer 604, and a second layer 606. As shown, the first layer 604 may include a high index material and the second layer 606 may include a low index material. In other embodiments, the first layer 604 may include a low index material and the second layer may include a high index material. Additionally, the first layer 604 is shown adjacent the substrate 602. In other embodiments, the first layer 604 may have another layer (for example, second layer 606 and/or another layer) between the substrate 602 and the first layer 604. Additional layers are also shown (though not numbered). The substrate 602 may utilize any substrate described herein. For example, the substrate 602 may include a tinted layer (not shown) on the same and/or opposite side of the first layer 604 and second layer 606 (i.e. the front and/or back side of the substrate). In another example, the substrate 602 itself may be impregnated with tint. Examples of tinting techniques and amounts are described below. Other embodiments of multi-layer filters are further described herein.

A filter 700, shown in FIG. 7, includes a substrate 702, a host layer 704, and a plurality of nanoparticles 706. The host layer 704 is shown adjacent the substrate 702. In other embodiments, the host layer 704 may have another layer (for example, second layer 606 from FIG. 6 and/or another layer) between the substrate 702 and the host layer 704. Although the nanoparticles 706 are shown as spherical and uniformly sized, as described above, other shapes and sizes are contemplated. As with the multi-layer filter of FIG. 6, various substrates, tints, other features, or combinations thereof may be used with the nanoparticle filter 700. Other embodiments of nanoparticle filters are described herein.

Other types of filters that may be used may include color filters (organic dye and semiconductor), resonant guided-mode filters, rugate filters, or combinations thereof. A rugate filter utilizes a sinusoidal refractive index variation throughout its thickness. A true sinusoid may not be obtainable and is often approximated by a staircase refractive index approximation using the mixture of two or more materials.

In addition to these various filter types, further considerations may take into account the effect of the designed filter on the visual response spectrum, as determined by the photoresponse of the rods and cones. One consideration may include minimizing spectral distortion. Adding additional or other constraints on filter design may be considered, including optimization methods, such as taking angular sensitivity into account, which can be compensated for, using dielectric multi-layers, for example, when attenuating light near 480 nm approaching melanopsin ganglion cells, by designing the center of the notch to be slightly red-shifted from about 480 nm to account for the blue-shift of the filter response that occurs for off-axis illumination. Depending on the wavelength attenuated, the degree of red-shift or blue-shift may vary. Optimization may further include widening the filter spectral width to compensate for non-normal incidence angles, and/or through the use of additional filter layers to compensate for angle of incidence. The potential for backside reflection may be a consideration. One or more of these considerations may be addressed by combining the filter with some form of tinting.

One embodiment of a method for manufacturing an optical filter to block light absorption by melanopsin cells is described herewith. The light dose D experienced by melanopsin cells can be written $$D_{melan} = \int L(\lambda) T(\lambda) M(\lambda) d\lambda \quad (1)$$

where L is the light spectrum (in terms of intensity, power, photons/sec, etc.), T is the spectral transmission of a filter lying between the light source and the eye, and M is the normalized action potential response spectrum of melanopsin, as currently estimated from FIG. 1 as a Gaussian function centered at 480 nm with a full-width at half-maximum of 52 nm. For generality, it is assumed that L=1 so as not to limit discussion to any specific light source, however analyses may be performed for any light source of known spectrum.

A similar dose can be calculated in association with the visual response spectrum $$D_{vis} = \int L(\lambda) T(\lambda) V(\lambda) d\lambda \quad (2)$$

where V represents the normalized visual response spectrum.

The effect of an optical filter, such as the FL-41 tint, is to reduce the dose, as described by taking the ratio of dose calculated with the filter to dose without the filter, for example $$N_{melan} = \frac{D_{melan}}{D_{melan}(T=1)}$$

The "attenuation" of the dose may be written as, for example, $$A_{melan} = 1 - N_{melan} = 1 - \frac{D_{melan}}{D_{melan}(T=1)}$$

A figure of merit (FOM) can also be defined which compares the blocking of the melanopsin response to the blocking of the visual response spectrum $$FOM = \frac{1 - \frac{D_{melan}}{D_{melan}(T=1)}}{1 - \frac{D_{vis}}{D_{vis}(T=1)}} \quad (3)$$

which represents the ratio of the attenuation of light across the melanopsin spectrum to the attenuation of light across the visible spectrum, where a value of FOM>1 may be desirable. For the FL-41 tint, FOM is about 1.

Figure 8:
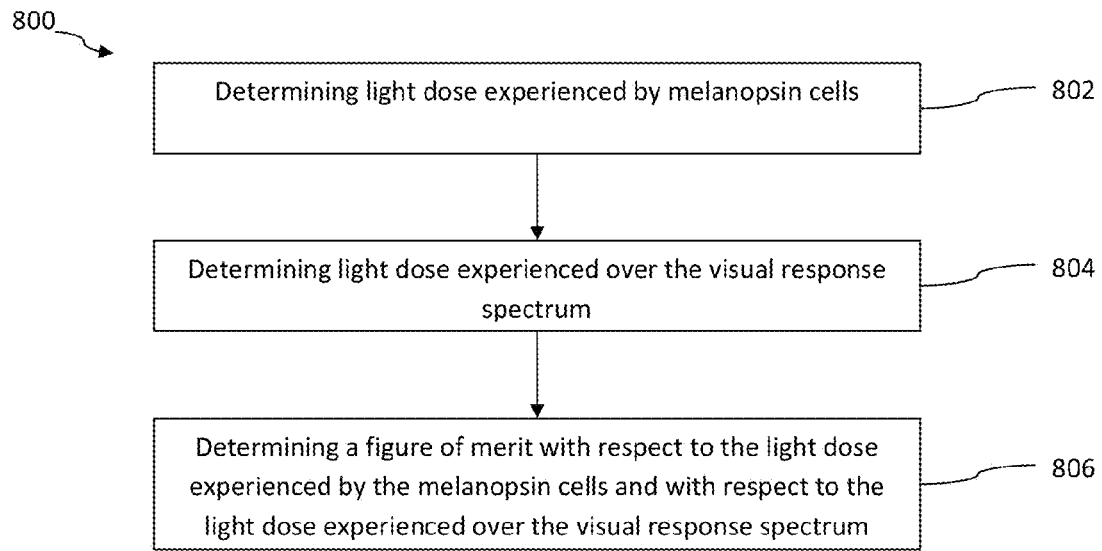
FIG. 8 illustrates an exemplary method for designing an optical filter to block light absorption by melanopsin cells

FIG. 8 illustrates one embodiment of a method 800 for designing an optical filter to block light absorption by melanopsin cells that may include determining the light dose D experienced by melanopsin cells (using, for example, Equation 1), as illustrated by act 802. The light dose experienced across the visual response spectrum may be determined (using, for example, Equation 2), as illustrated by act 804. A figure of merit (FOM) may be determined with respect to the light dose experienced by the melanopsin cells and to the light dose experienced across the visual response spectrum, as illustrated by act 806. In other embodiments, the dose across the visual response spectrum may be reduced or separated. For example, only a portion or portions of the visual response spectrum may be used, or wavelengths outside the visual response spectrum may be considered. The figure of merit may be used to design an optical element to reduce and/or prevent photophobic responses.

Many embodiments described herein use multi-layer dielectric thin films of distinct refractive indices. These layers may be applied to a number of optical elements (as described herein). By way of example, and in no way intended to be limiting, embodiments of optical filter designs of the present disclosure assume a generic transparent substrate, such as a spectacle lens, with refractive index around 1.5, and with an anti-reflection coating applied to the back surface (i.e. the surface closest to the user's eye). Thus, other substrates with other refractive indices, and with or without back surface anti-refection coatings, are contemplated. Minor variations in filter design may be required to compensate for different substrate materials and/or different coatings on those substrates. Further considerations may need to be addressed such as compatibility of different thin-film materials with different substrate materials, which may require further design optimization, and the curvatures of the lens substrate. The substrate may include an adhesion layer (for example a thin layer of chromium) between the substrate, or a layer on the substrate, and any further coatings.

There are a multitude of design approaches to multi-layer long-pass and notch filters which may be used. For example, software and other design tools are available for the design of thin film optical filters. These tools may take a number of constraints into account during optimization, reducing the likelihood that any two filter designs will be identical, even if accomplishing the same light blocking characteristics or producing the same physiological result. Only a few examples will be presented here and are not meant to be limiting in any way. Other approaches could be taken to achieve similar results, and further optimizations could be performed in order to produce more ideal characteristics, or to produce similar characteristics with fewer number of layers, in accordance with the present disclosure.

In addition, multi-layer and other coatings may be applied to tinted lenses or substrates. There are multiple reasons why this combination may be desirable. One reason may include that the spectral characteristics of the tint may relax design constraints on the thin film filter. For example, combining an FL-41 "base tint" with a thin-film notch filter may serve to reduce the depth of the notch necessary to produce a therapeutic outcome. It may be desirable to take into account the spectral variation of transmission of the tint in the notch design. This design adjustment may be accomplished by, for example, shifting the center wavelength of the notch to compensate for the local slope of the tint spectral response. Another reason for using a base tint may be to reduce any undesirable reflection of light that enters though the backside of the lens. In this situation, it may be desirable to use a "flat," or neutral density, tint that would not introduce any coloration in and of itself.

For example, in an embodiment of a filter designed to block a range of wavelengths of light from passing through the front of the lens (by, for example, reflecting the desired wavelengths away from the user), the light entering the back side of the lens (which includes light in the wavelengths to be blocked) may be reflected back into the user's eye. In other words, the light to be blocked from the front (by reflection in the case of a multi-layer filter) may then be reflected from the back. This may not be a concern in situations where there is a single light source that is mainly in front of the subject. However, in situations, for example, where very bright light is found or where there are multiple light sources, this back reflection may be deleterious to the user.

One example approach to producing long pass or notch filters includes using alternating layers of high and low refractive index materials. Example low index dielectric materials include $MgF_2$ and $SiO_2$. $MgF_2$ is commonly used in single and multi-layer anti-reflection coatings. Example high index materials include metal oxides such as $TiO_2$, $Ti_3O_5$, $ZrO_2$, and $Ta_2O_5$, and $Si_3N_4$. Numerous other suitable materials can be used, including polymer layers.

Figure 9:
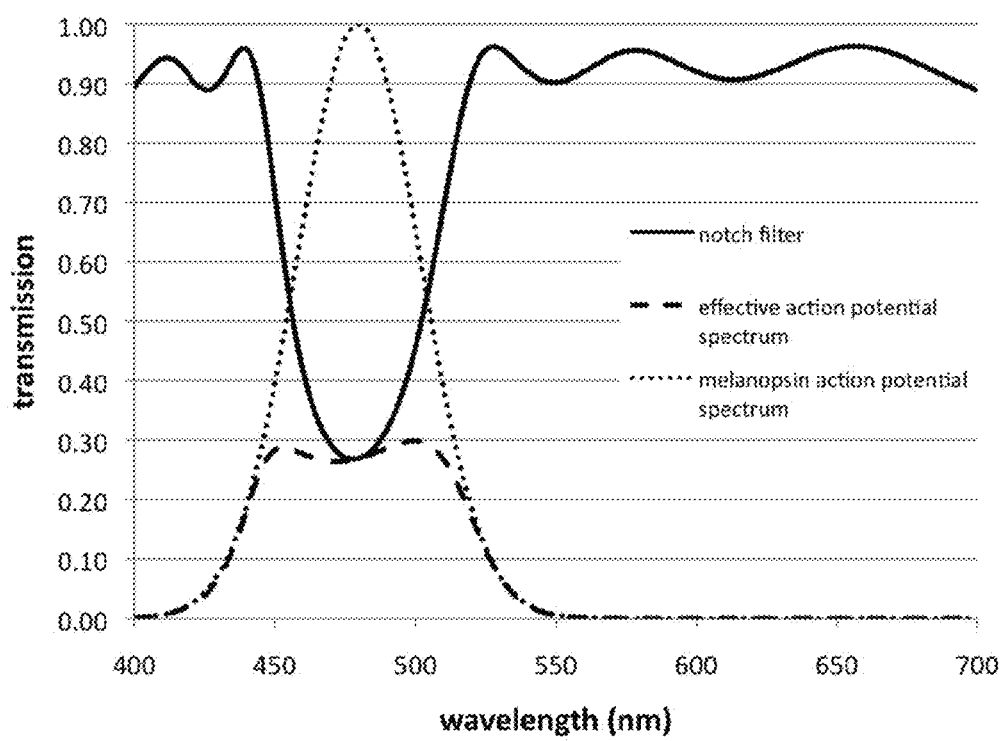
FIG. 9 illustrates the measured transmission spectrum of one embodiment of a filter across the "effective action potential spectrum" of melanopsin.
Figure 10:
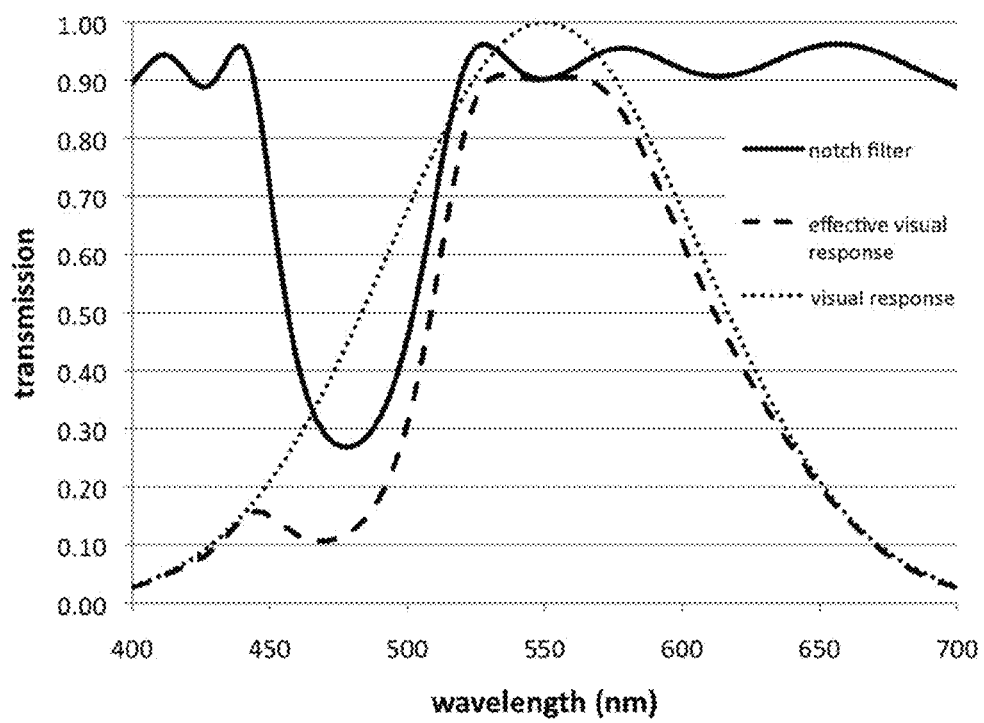
FIG. 10 illustrates the measured transmission spectrum of the embodiment of a filter in FIG. 9 across the visible light spectrum.

Optical filters for attenuating light near various wavelengths, such as 480 nm, 620 nm, or other specific wavelengths, may follow similar designs. One embodiment of an optical filter design is shown in FIGS. 9 and 10, along with the effect of this embodiment of a filter on the spectrum of light that strikes melanopsin cells, producing an effective (and attenuated) action potential. This design is intended to be as clinically effective as the FL-41 35 coating, in that 55% of the light that would be absorbed by melanopsin cells is blocked, or attenuated, which should result in the same alleviation of migraine (or light sensitive) symptoms as the FL-41 coating, but with significantly less visual distortion, with only 18% attenuation across the visual response. For this embodiment, the low index material is $SiO_2$ and the high index material $TiO_2$, and $MgF_2$ is used as the outermost layer, and 11 total layers are used. Exemplary layers and materials are listed in the table below from the outermost layer ($MgF_2$) to the innermost layer ($TiO_2$ with 165 nm thickness) adjacent to the substrate. This filter has FOM≈3.

| Material | Thickness (nm) |
| --- | --- |
| $MgF_2$ | 126 |
| $SiO_2$ | 212 |
| $TiO_2$ | 125 |
| $SiO_2$ | 134 |
| $TiO_2$ | 129 |
| $SiO_2$ | 62 |
| $TiO_2$ | 12 |
| $SiO_2$ | 51 |
| $TiO_2$ | 26 |
| $SiO_2$ | 40 |
| $TiO_2$ | 165 |

The spectral position of the center of a notch filter may be determined by the thicknesses of its respective layers. Although many embodiments herein assume the spectral position of the notch is at about 480 nm, other spectral positions are contemplated. For example, as more information about the action potential spectrum of the melanopsin pathway is known, the spectral position may be shifted in accordance with the new information, such as to 620 nm. In another example, the spectral position may be otherwise positioned to achieve specific results, such as to attenuate wavelengths other than those of the action potential spectrum of the melanopsin pathway.

The width of the notch may be determined by the difference in refractive indices of the different layers. The depth of the notch may be determined by the number of layers. The transmission outside of the notch region may be increased and flattened through the inclusion of additional layers, and with the possible inclusion of a single or multi-layer anti-reflection coating applied to the back surface of the lens to reduce backside reflection. Further design optimization can be used to increase the depth of the notch which may further suppress excitation of melanopsin cells, but the effect on the visual response spectrum should be considered. Overall suppression may be tailored on a patient-by-patient basis or by designing one or more general classes of filters in order to help the majority of cases.

Figure 11:
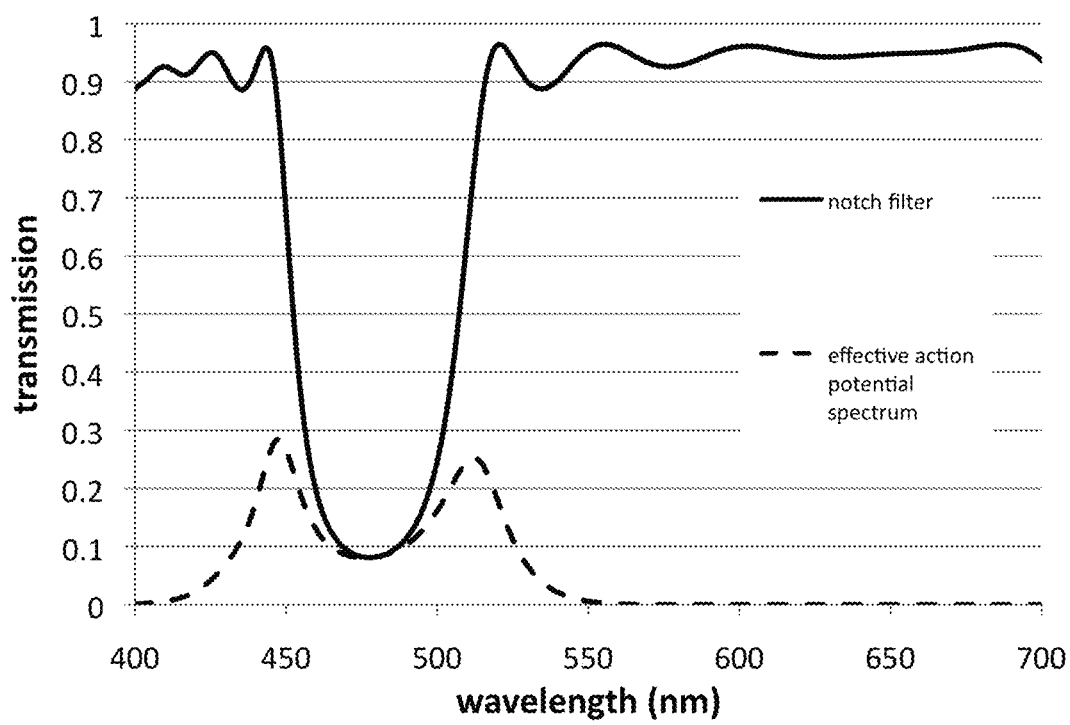
FIG. 11 illustrates the measured transmission spectrum of another embodiment of a filter across the "effective action potential spectrum" of melanopsin.
Figure 12:
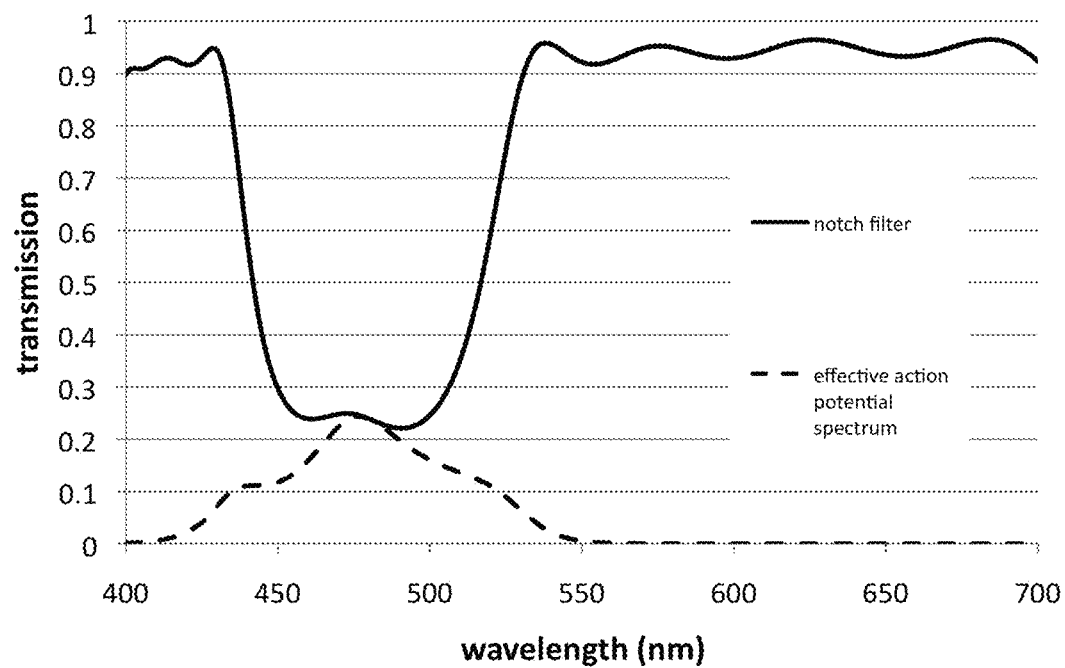
FIG. 12 illustrates the measured transmission spectrum of a further embodiment of a filter across the "effective action potential spectrum" of melanopsin.

Greater attenuation of the effective melanopsin action potential spectrum may be obtained by either deepening or widening the filter notch, or through a combination of both. FIGS. 11 and 12 illustrate embodiments of two exemplary approaches, using 19 and 15 dielectric layers, respectively. The ultimate choice between the two can be made based upon wearer preference, as both produce about a 70% attenuation across the melanopsin spectrum, but have slightly different visual response spectrum characteristics. The 19 layer filter attenuates about 21% of the visual response spectrum, and the 15 layer filter attenuates about 25% of the visual response spectrum. Both filters have FOM values greater than 2.75, with the 19 layer filter having an FOM value of about 3.3.

Figure 13:
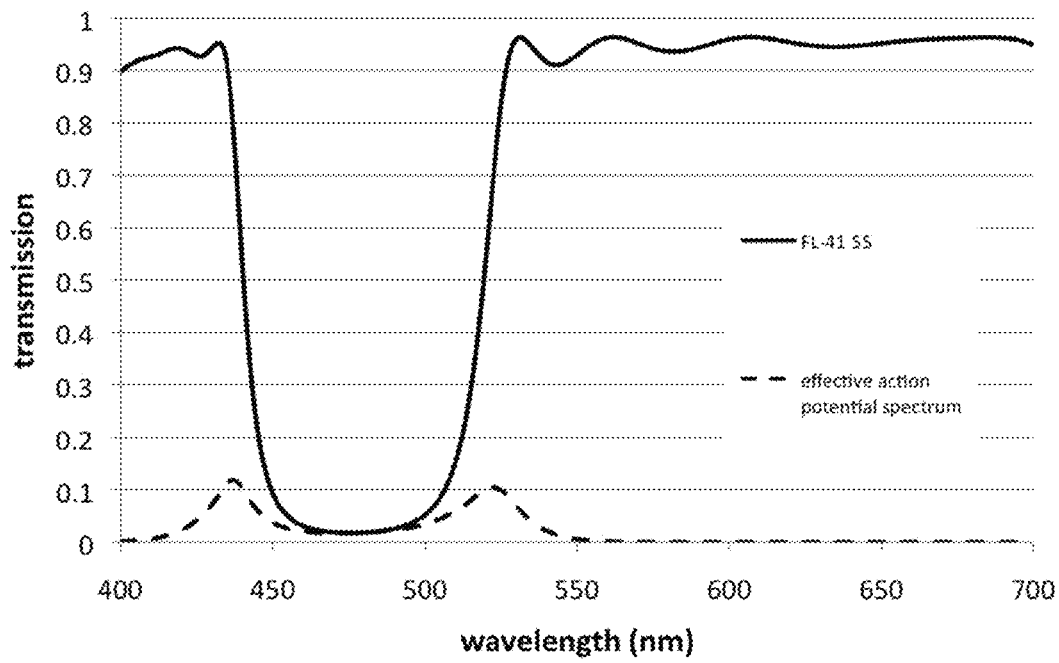
FIG. 13 illustrates the measured transmission spectrum of a still further embodiment of a filter across the "effective action potential spectrum" of melanopsin.
Figure 14:
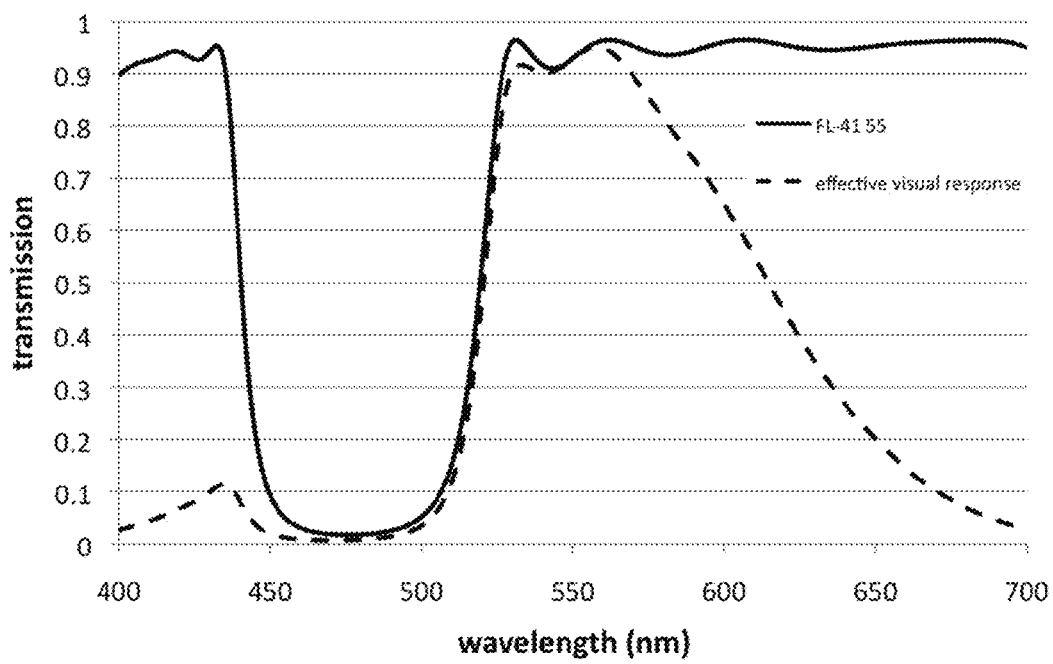
FIG. 14 illustrates the measured transmission spectrum of the embodiment of a filter in FIG. 13 across the visible light spectrum.

Different designs may achieve significant attenuation across the melanopsin action potential spectrum. FIGS. 13 and 14 show an embodiment of a notch filter design that produces a melanopsin action potential attenuation similar to the FL-41 55 filter, blocking about 89% of the light, using 19 dielectric layers, but blocking only about 29% of the visual response spectrum, with an FOM value of about 3. Exemplary layers and materials are listed in the table below from the outermost layer ($MgF_2$) to the innermost layer ($TiO_2$ with 160.3 nm thickness) adjacent to the substrate.

| Material | Thickness (nm) |
| --- | --- |
| $MgF_2$ | 179.9 |
| $SiO_2$ | 152.3 |
| $TiO_2$ | 75.8 |
| $SiO_2$ | 16.9 |
| $TiO_2$ | 80.5 |
| $SiO_2$ | 35.1 |
| $TiO_2$ | 38.0 |
| $SiO_2$ | 128.6 |
| $TiO_2$ | 66.5 |
| $SiO_2$ | 17.7 |
| $TiO_2$ | 55.5 |
| $SiO_2$ | 67.5 |
| $TiO_2$ | 88.3 |
| $SiO_2$ | 22.0 |
| $TiO_2$ | 63.1 |
| $SiO_2$ | 30.7 |
| $TiO_2$ | 84.2 |
| $SiO_2$ | 34.8 |
| $TiO_2$ | 160.3 |

Other design considerations may include blocking for light that strikes at non-normal incidence angles. For instance, tilting the angle of a thin film filter tends to produce a blue-shift in the filter response. This may be accommodated, for example, by either purposefully designing the filter with a slight red shift, by broadening the width of the filter, adding additional layers, or combinations thereof to minimize or reduce the effect of the angle of incidence.

Figure 15:
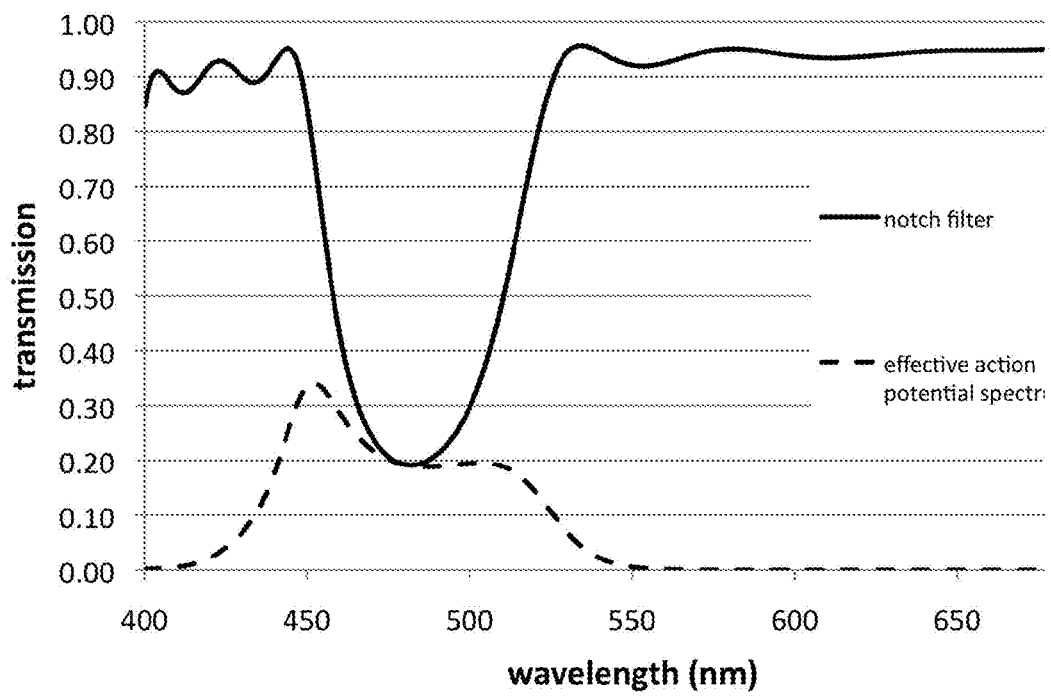
FIG. 15 illustrates the measured transmission spectrum of an even further embodiment of a filter with the center of the filter positioned at 485 nm for normal light incidence across the "effective action potential spectrum" of melanopsin.

FIG. 15 shows an embodiment of a filter design with 10 layers, where the center of the notch is positioned at 485 nm for normal light incidence. At normal incidence, this embodiment of a filter blocks about 61% of the light dose to the melanopsin spectrum and only attenuates about 21% of the light to the visual response spectrum, resulting in an FOM value of about 2.9.

Figure 16:
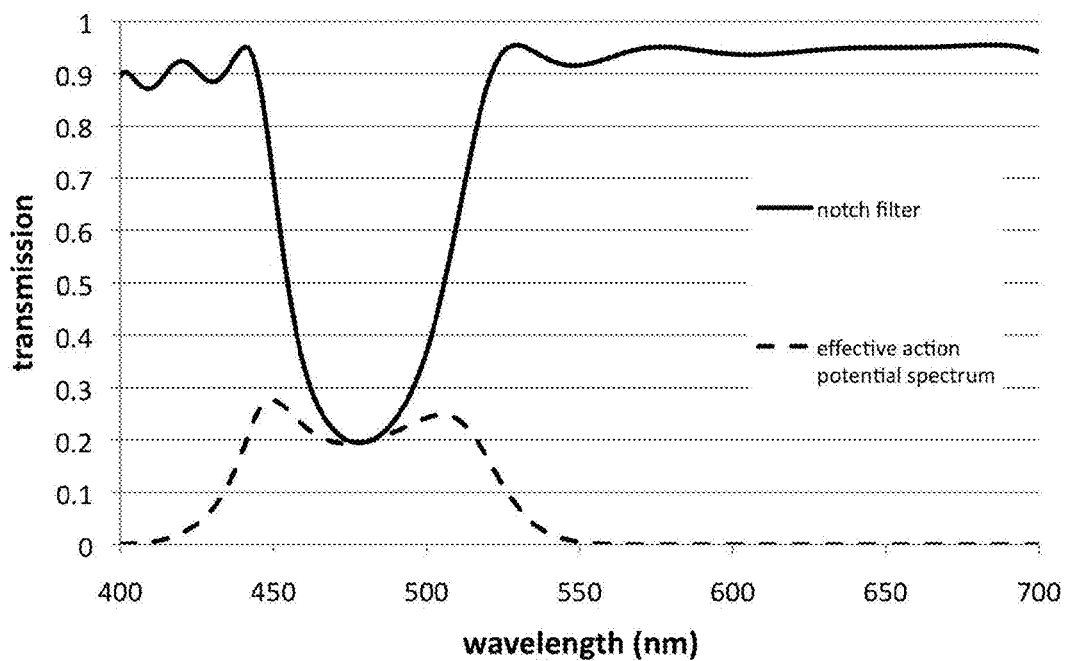
FIG. 16 illustrates the measured transmission spectrum of the embodiment in FIG. 15 with an incidence angle of 15 degrees across the "effective action potential spectrum" of melanopsin.

FIG. 16 shows the effect of the embodiment of a filter from FIG. 15, but with an incidence angle of about 15 degrees. In this embodiment and at this incidence angle, blocking of the melanopsin light dose is about 61% with about 20% blocking of the visual response spectrum, resulting in an FOM value of about 3.1.

This embodiment of a filter has the following layer properties listed in the table below from the outermost layer ($MgF_2$) to the innermost layer ($TiO_2$ with 127 nm thickness).

| Material | Thickness (nm) |
|---|---|
| $MgF_2$ | 117 |
| $TiO_2$ | 88 |
| $SiO_2$ | 190 |
| $TiO_2$ | 78 |
| $SiO_2$ | 192 |
| $TiO_2$ | 90 |
| $SiO_2$ | 37 |
| $TiO_2$ | 140 |
| $SiO_2$ | 134 |
| $TiO_2$ | 127 |

Figure 17:
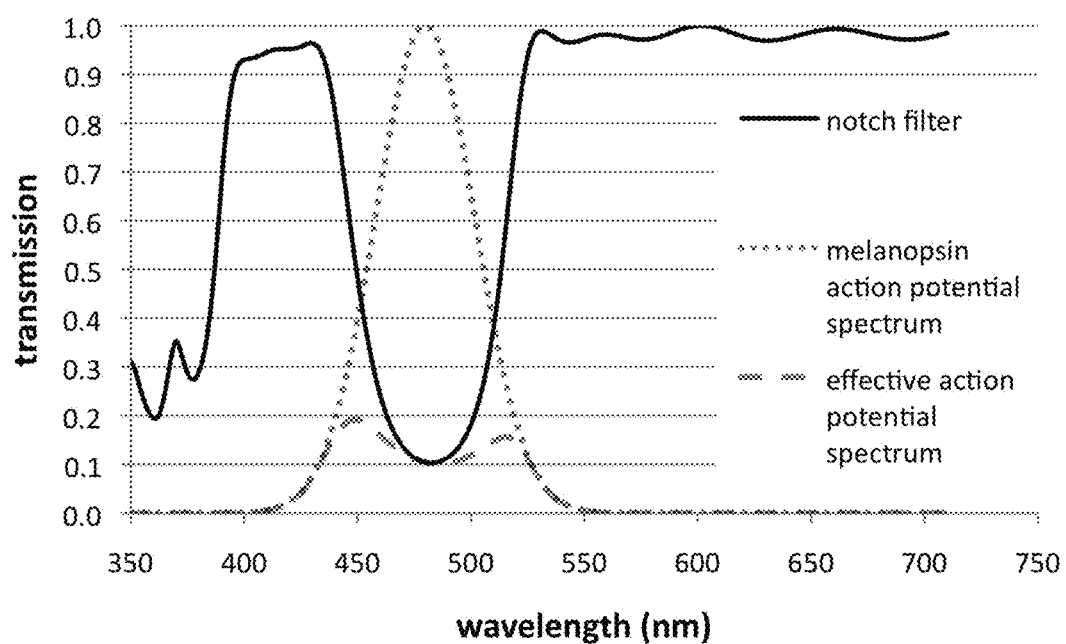
FIG. 17 illustrates the measured transmission spectrum of a yet further embodiment of a filter excluding a low-index $MgF_2$ layer across the "effective action potential spectrum" of melanopsin.

In the embodiments of filters described in connection with FIGS. 8-15, a low-index $MgF_2$ layer was used. Other embodiments may not require this material. For example, FIG. 17 illustrates an embodiment of filter design which blocks about 73% of the melanopsin action potential spectrum (or light dose) and about 21% of the dose of the visible response, with an FOM value of about 3.5. The layer properties of the filter design illustrated in FIG. 17 are listed in the table below from the outermost layer to the innermost layer.

| Material | Thickness (nm) |
|---|---|
| $SiO_2$ | 58.6 |
| $TiO_2$ | 117.0 |
| $SiO_2$ | 138.0 |
| $TiO_2$ | 57.4 |
| $SiO_2$ | 18.8 |
| $TiO_2$ | 41.9 |
| $SiO_2$ | 128.5 |
| $TiO_2$ | 149.9 |
| $SiO_2$ | 52.1 |
| $TiO_2$ | 161.1 |
| $SiO_2$ | 187.7 |
| $TiO_2$ | 5.4 |
| $SiO_2$ | 45.9 |
| $TiO_2$ | 264.9 |
| $SiO_2$ | 33.1 |
| $TiO_2$ | 9.9 |
| $SiO_2$ | 208.5 |

As discussed above, it may be desirable to reduce the amount of light that is reflected from the back side (i.e. the side closest to the user's eye) into the user's eye. This may be accomplished by another embodiment of a filter design in which a thin film coating may be applied onto a tinted lens or substrate. In other embodiments, the substrate may be tinted by impregnation, coating, other tinting techniques, or combinations thereof. The transmission of light through a thin-film coating/tinted substrate combination may be written as the product of the transmission of the thin-film coating and the transmission of the tinted substrate:

$$T(\lambda)=T_{film}(\lambda)T_{tint}(\lambda) \quad (4)$$

assuming that the thin-film coating is applied only to the front surface of the substrate and assuming that an anti-reflection coating (with T≈1) is applied to the back surface of the substrate.

For light entering the back surface of the substrate, it first passes through the tint, is reflected from the thin-film filter on the front surface of the substrate, then passes through the tint a second time before striking the user's eyes. For this situation, the reflected light may be written $$R(\lambda)=T_{tint}(\lambda)[1-T_{film}(\lambda)]T_{tint}(\lambda)=R_{film}(\lambda)T_{tint}^2(\lambda)=T_{tint}(\lambda)[T_{tint}(\lambda)-T(\lambda)] \quad (5)$$

At any particular wavelength, the fraction of light transmitted and reflected may be set by the transmission of the thin film coating and tint. For example, if about 20% transmission is desired at a desired wavelength (in this example about 480 nm), then only certain combinations of thin film and tint transmissions may be used. Furthermore, if about 10% reflection is desired, then only a single combination of thin film and tint transmissions is allowed. These relationships may be described as follows:

$$T_{tint}^2(\lambda)-(\lambda)T_{tint}(\lambda)-R(\lambda)=0 \quad (6)$$

$$T_{film}(\lambda) = \frac{T(\lambda)}{T_{tint}(\lambda)} \quad (7)$$

The dose D experienced by melanopsin cells due to back reflected light into the user's eyes can be written similarly to the dose experienced by melanopsin cells due to transmitted light shown in Equation (1)

$$D_{R-melan}=\int L(\lambda)R(\lambda)M(\lambda)d\lambda \quad (8)$$

where L is the light spectrum (in terms of intensity, power, photons/sec, etc.), R is the spectral back reflection, and M is the normalized action potential response spectrum of melanopsin, as currently estimated from FIG. 1 as a Gaussian function centered at 480 nm with a full-width at half-maximum of 52 nm. For generality, it is assumed that L=1 so as not to limit discussion to any specific light source, however analyses may be performed for any light source of known spectrum.

The normalized dose by back reflected light experienced by melanopsin cells may be calculated by $$N_{R-melan} = \frac{D_{R-melan}}{D_{melan}(T=1)} \quad (9)$$

A similar dose and normalized dose can be calculated in association with the visual response spectrum $$D_{R-vis} = \int L(\lambda)R(\lambda)V(\lambda)d\lambda \quad (10)$$

$$N_{R-vis} = \frac{D_{R-vis}}{D_{vis}(T=1)} \quad (11)$$

where V represents the normalized visual response spectrum. Ideally, backreflection would be reduced so that these dose values are close to zero.

The dose of back reflected light with respect to the action potential spectrum of the melanopsin pathway may be determined using Equation (8). The dose of back reflected light with respect to the visual spectrum may be determined using Equation (9). The doses of back reflected light may be used to design and manufacture an optical filter. For example, an appropriate level of tinting may be selected based on the maximum desired dose of back reflected light, whether across the action potential spectrum of the melanopsin pathway, across the visual spectrum, or both. Reduction of the dose and normalized dose of back reflected light experienced by melanopsin cells may reduce the symptoms experienced by a photophobic user.

The following tables illustrate additional embodiments of filter designs with some possible combinations of notch and tint transmissions that result in specific transmissions and backside reflections at, for example, about 480 nm. Note that, due to the notch response, the transmission of light outside the notch will be greater than the transmission of light within the notch, so that the amount of back reflected light will be less than occurs at the notch center. Although these examples are specific to a notch centered near 480 nm, other wavelengths may be selected as described herein.

Table 1 provides examples that maintain a fixed 10% backside reflection at a specific wavelength (around 480 nm, for example) or range of wavelengths, with different transmissions through the frontside. This value of backside reflection might be desirable for therapeutic lenses that may be used in "open" style spectacle frames, for example, where light is allowed to strike the lenses from the top, bottom, and/or sides, thereby entering the backside of the lens and reflecting into the eyes of the user from the front-side thin-film coating. Other amounts of backside reflection may be desirable for other style spectacle frames (such as sport glasses, wraparound sunglasses, or other styles of frames).

TABLE 1

| transmission T | back refl R | $T_{tint}$ | $T_{film}$ |
|---|---|---|---|
| 0.50 | 0.10 | 0.65 | 0.77 |
| 0.45 | 0.10 | 0.61 | 0.73 |
| 0.40 | 0.10 | 0.57 | 0.70 |
| 0.35 | 0.10 | 0.54 | 0.65 |
| 0.30 | 0.10 | 0.50 | 0.60 |
| 0.25 | 0.10 | 0.47 | 0.54 |
| 0.20 | 0.10 | 0.43 | 0.46 |
| 0.15 | 0.10 | 0.40 | 0.38 |
| 0.10 | 0.10 | 0.37 | 0.27 |

Table 2 provides further embodiments, but with greater backside reflection allowed. These designs may be more appropriate for "wrap" style spectacle or sport frames, which prevent light from entering the eyes except for that light which passes through the front-side of the lenses.

TABLE 2

| transmission T | back refl R | $T_{tint}$ | $T_{film}$ |
|---|---|---|---|
| 0.50 | 0.35 | 0.89 | 0.56 |
| 0.45 | 0.35 | 0.86 | 0.52 |
| 0.40 | 0.35 | 0.82 | 0.49 |
| 0.35 | 0.35 | 0.79 | 0.44 |
| 0.30 | 0.35 | 0.76 | 0.39 |
| 0.25 | 0.35 | 0.73 | 0.34 |
| 0.20 | 0.35 | 0.70 | 0.29 |

TABLE 2-continued

| transmission T | back refl R | $T_{tint}$ | $T_{film}$ |
|---|---|---|---|
| 0.15 | 0.35 | 0.67 | 0.22 |
| 0.10 | 0.35 | 0.64 | 0.16 |

Other embodiments of a filter may include fixing the notch transmission and adjusting the tint transmission to provide a given backside reflection value. Examples of these embodiments are shown in Table 3 below.

TABLE 3

| transmission $T_{film}$ | back refl R | $T_{tint}$ | trans T |
|---|---|---|---|
| 0.35 | 0.05 | 0.28 | 0.10 |
| 0.35 | 0.10 | 0.39 | 0.14 |
| 0.35 | 0.15 | 0.48 | 0.17 |
| 0.35 | 0.20 | 0.55 | 0.19 |
| 0.35 | 0.25 | 0.62 | 0.22 |
| 0.35 | 0.30 | 0.68 | 0.24 |
| 0.35 | 0.37 | 0.75 | 0.26 |
| 0.25 | 0.45 | 0.77 | 0.19 |
| 0.15 | 0.50 | 0.77 | 0.12 |

The R values described herein may be used to determine the maximum amount of back reflected light. For example, an R value of about 0.10 could be used as a desired amount of back reflected light weighted across the action potential spectrum of the melanopsin pathway, the visual spectrum, or both. As the R values are based on a desired wavelength to attenuate, other wavelengths of light may be attenuated based on a filter designed to achieve an R value equal to or less than values according to the tables above. For example, for a wavelength of about 480 nm with an R value of about 0.10, the R value for a wavelength of about 470 nm or 490 nm may be less than 0.10, such as about 0.09. R values will generally decrease at wavelengths away from the desired notch center wavelength. For clarity, though the tables herein list the R value as a decimal value, these values may also be expressed as percentages.

These examples are not intended to limit the combinations appropriate for the present disclosure and are provided only to demonstrate some of the possible combinations that may be appropriate for therapeutic effects. Any number of other combinations are envisioned and may be appropriate for different levels of user light sensitivity, for different diseases, for different applications, and for different types of tints (e.g. gray, FL-41, etc.), and different frame styles.

Manufacturing considerations may also be taken into account when performing filter design. For example, material deposition is typically accomplished using sputtering, evaporation, or chemical vapor deposition techniques. Deposition conditions may be optimized to minimize stress of the thin film materials. Oftentimes high temperature thermal annealing may be performed post-deposition to relax stress in the deposited materials, but annealing often cannot be applied to plastic lenses. Spectacle lenses represent curved substrates, so that achieving constant film thickness during deposition may be a challenge. To produce constant film thicknesses, modification of the target-source geometry in the deposition system may be used. For plastic lenses, low temperature deposition may be used, but may be optimized to produce low stress films.

Figure 18A:
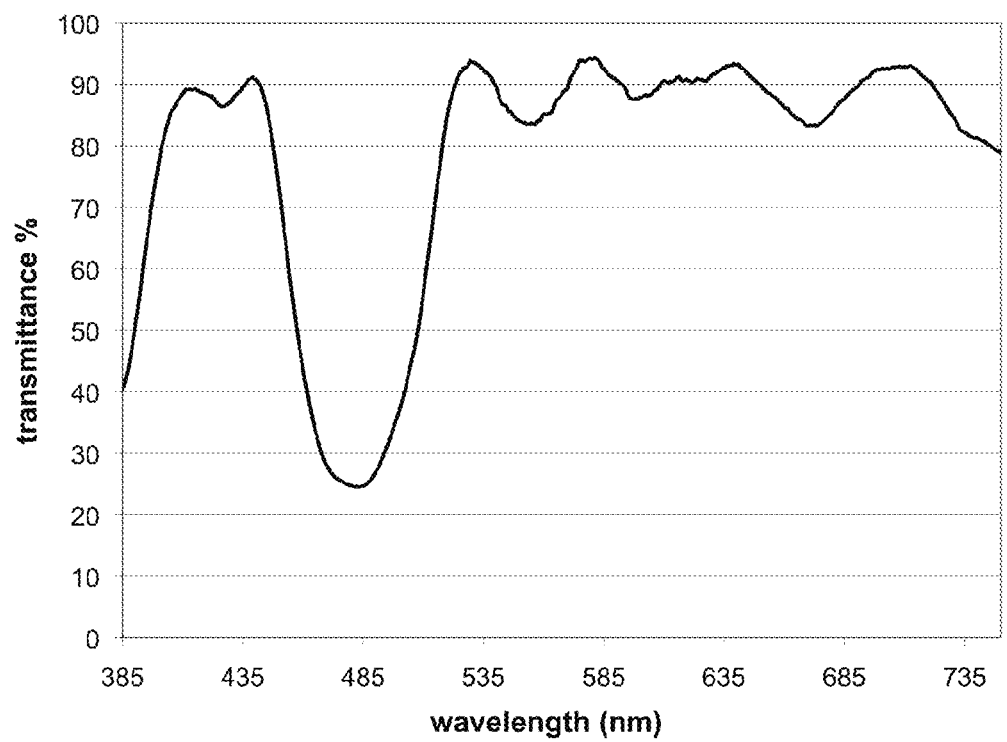
FIGS. 18A and B illustrate the measured transmission spectrum of an embodiment of a filter centered at about 480 nm and an embodiment of a filter centered at about 620 nm.
Figure 18B:
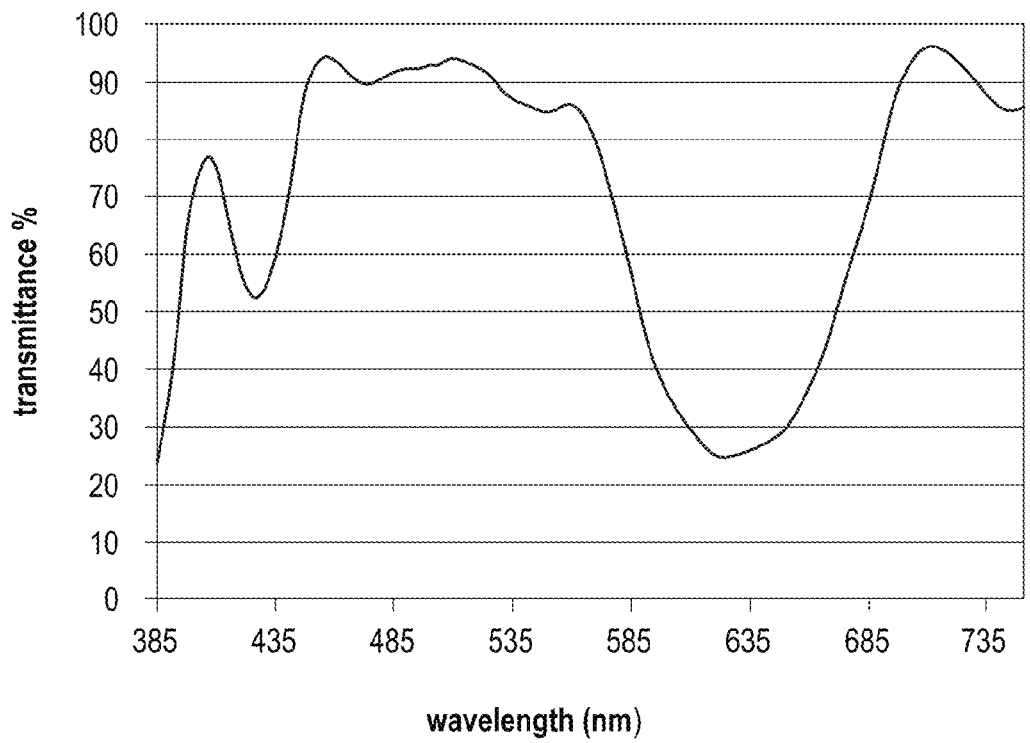

The following working examples describe tested optical filter designs and their results. Test notch coatings were produced on polycarbonate or CR-39 plano lenses with scratch resistant coatings. A thin layer of Cr was deposited on to the substrate to act as an adhesion layer for the thin film stack. The transmission spectrum through an example coated lens is shown in FIG. 18A. The center of the notch is at about 482.9 nm with width of about 55.5 nm, with minimum transmittance of about 24.5%. This embodiment of a filter blocks about 58% of the melanopsin action potential spectrum and blocks about 23% across the visible spectrum, with an FOM value of about 2.6. In contrast, FIG. 18B depicts a transmission spectrum of a coated lens with a 620 nm notch filter.

In a preliminary clinical trial, migraine sufferers were recruited to wear spectacles with the therapeutic notch coating of FIG. 18A. Participants wore therapeutic lenses for 2 weeks. For inclusion in the trial, all participants reported chronic daily headache, defined as more than 15 days with headache per month. A validated questionnaire, HIT6, was used to assess the effects of headaches on the participants' daily lives, both before and after wearing the therapeutic lenses. A tabulation of the HIT6 scores is shown in the following table. An average of about 6.6% improvement was obtained, consistent with a significant improvement in quality of life for the participants.

| Participant | HIT6 before | HIT6 after | Improvement |
| --- | --- | --- | --- |
| #1 | 61 | 57 | 6.6% |
| #2 | 76 | 68 | 11% |
| #3 | 65 | 62 | 4.6% |
| #4 | 55 | 48 | 13% |
| #5 | 70 | 68 | 2.9% |
| #6 | 69 | 65 | 5.8% |
| #7 | 61 | 58 | 4.9% |
| #8 | 63 | 60 | 4.8% |
| #9 | 69 | 60 | 13% |
| #10 | 68 | 67 | 1.5% |
| #11 | 68 | 65 | 4.4% |

Figure 19:
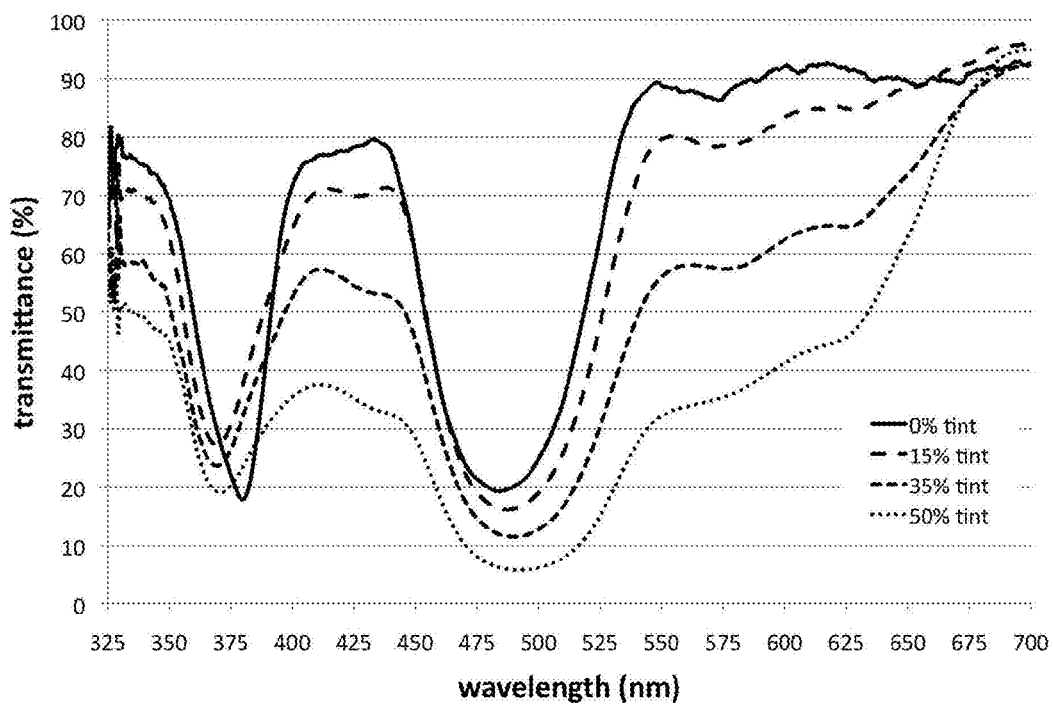
FIG. 19 illustrates the measured transmission spectrum of multiple embodiments of filters centered at about 480 nm with varying degrees of tint.
Figure 20:
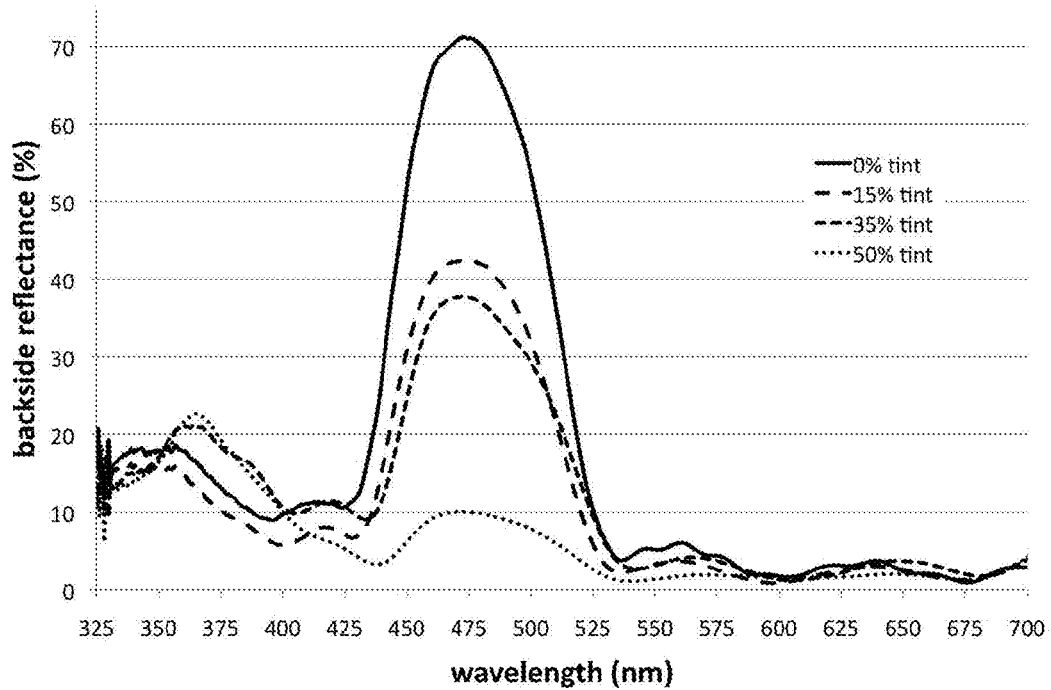
FIG. 20 illustrates the backside reflection spectra of the embodiments of filters in FIG. 19.

In another working example, thin film notch coatings have been applied to FL-41 tinted lenses. The transmission and backside reflection spectra are shown in FIGS. 19 and 20. Different levels of FL-41 tint were applied to tintable scratch resistant layers (also called hard coatings) on the polycarbonate or CR-39 lenses. The multi-layer notch filter was then applied to the front side of each lens, with a conventional anti-reflection coating applied to the backside of each lens. As can be seen from FIGS. 19 and 20, the FL-41 tint dramatically decreased the backside reflection. However, in the transmission, the notch response is red-shifted due to the slope of the FL-41 tint near 480 nm. This shift may be compensated for by starting with a slightly blue-shifted notch design.

The following table lists the blocking levels across the melanopsin and visual response spectrum and the FOM values for each tint level. Similar results can be expected by utilizing other tints, such as gray tints such as "sun gray" from BPI.

| FL-41 tint level | Melanopsin blocking | Visual blocking | FOM |
| --- | --- | --- | --- |
| 0% | 67.5% | 28.8% | 2.3 |
| 15% | 71.3% | 36.9% | 1.9 |
| 35% | 78.9% | 53.7% | 1.5 |
| 50% | 88.0% | 70.4% | 1.3 |

The coatings described here can also be integrated with other technologies. For example, filter coatings can be applied to tinted lenses, photochromic materials may be incorporated, techniques for polarization can be included, other technologies may be integrated, or combinations thereof. In addition, combinations of filter technologies may be used, such as applying a nanoparticle filter coating on top of a multi-layer thin-film coating. Active materials, such as electro-optic materials, including electro-optic polymers, liquid crystals, or other electro-optic materials, piezoelectric materials, including piezoceramics such as PZT, or other piezoelectric materials may be used.

Figure 21:
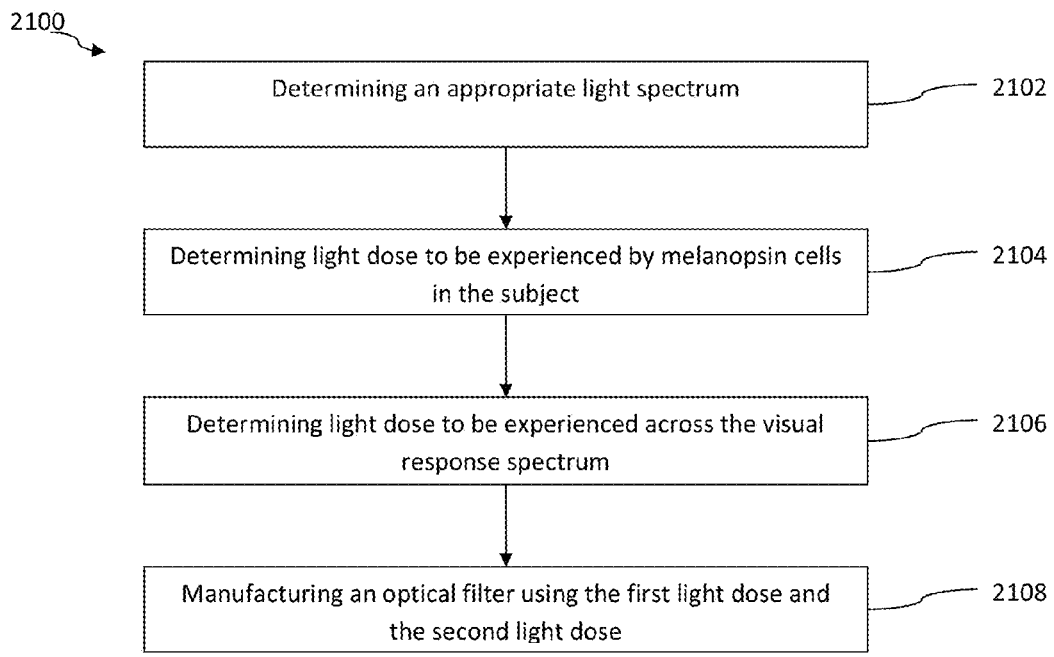
FIG. 21 illustrates an exemplary embodiment of a method of manufacturing an optical filter.

FIG. 21 illustrates an exemplary embodiment of a method 2100 of manufacturing an optical filter for reducing the frequency and/or severity of photophobic responses. The method 2100 may be used to design at least one embodiment of a filter described herein. The method 2100 may include determining the appropriate light spectrum, as illustrated by act 2102. Determining the appropriate light spectrum may include consideration of specific lighting conditions, such as taking spectrophotometric measurements, in conditions such as indoor fluorescent lighting and/or computer screens in an office, shopping, or home environment, or outdoor lighting such as sunlight experienced due to normal outdoor activities or sporting activities. The light dose to be experienced by melanopsin cells may be determined (using, for example, Equation 1), as illustrated by act 2104. The light dose to be experienced across the visual response spectrum may be determined (using, for example, Equation 2), as illustrated by act 2106. An optical filter may be designed and manufactured using the first light dose and the second light dose, as illustrated by act 2108. The first light dose and the second light dose may be used to determine a figure of merit (FOM) as described herein. In other embodiments, the dose across the visual response spectrum may be considered for a portion or portions of the visible spectrum. For example, more or less than the entire visual response spectrum may be used.

Figure 22:
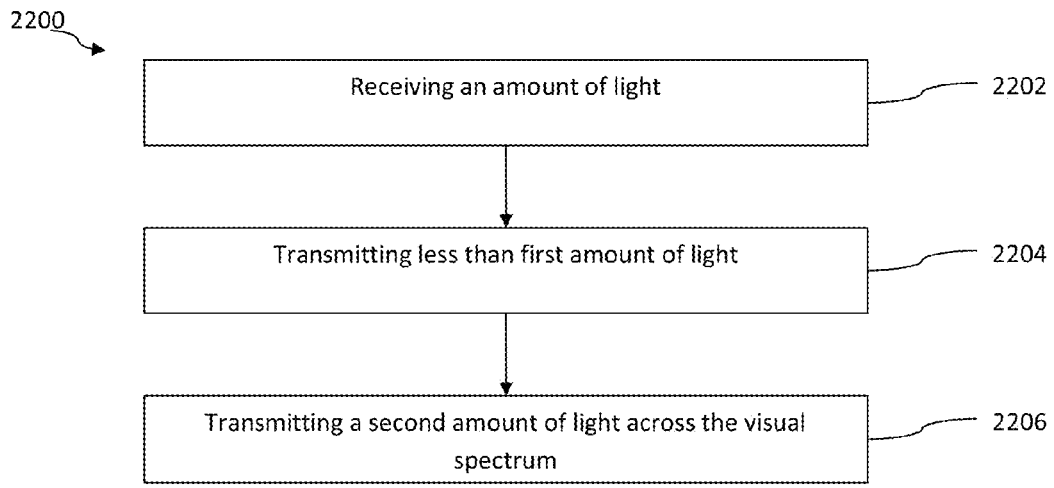
FIG. 22 illustrates an exemplary embodiment of a method for reducing the frequency and/or severity of photophobic responses or for modulating circadian cycles.

FIG. 22 illustrates an exemplary embodiment of a method 2200 for reducing the frequency and/or severity of photophobic responses or for modulating circadian cycles. The method 2200 may be used in conjunction with at least one embodiment of a filter described herein. The method 2200 may include receiving an amount of light, as illustrated by act 2202. The light received may include direct or indirect light from one or more light sources. Less than a first amount of light weighted across the action potential spectrum of the melanopsin cells may be transmitted, as illustrated by act 2204. A second amount of light weighted across the visual light spectrum may be transmitted, as illustrated by act 2206. An optical filter may be manufactured using the first light dose and the second light dose, as illustrated by act 2208. The first light dose and the second light dose may be used to determine a figure of merit (FOM) as described herein. In other embodiments, the dose across the visual response spectrum may be reduced or separated. For example, more or less than the entire visual response spectrum may be used.

In addition to regulating the exposure of melanopsin ganglion cells to light near 480 nm, it has been demonstrated through clinical testing that attenuation of light at a wavelength of about 620 nm may also yield improvements in alleviating symptoms associated with light sensitivity. Although light wavelengths at about 620 nm are not believed to act on the melanopsin ganglion cells, attenuation of light at about 620 nm has been demonstrated to reduce symptoms of light sensitivity in some people, such as pain or discomfort in response to light, and the frequency and/or severity of migraine and other headaches, and may also prove effective for some in the treatment of blepharospasm, post-concussion/TBI syndrome, sleep disorders, epilepsy.

In one embodiment, improvements may be realized by attenuating light between about 580 nm and about 650 nm. In another embodiment, improvements may be realized by attenuating light between about 600 nm and about 640 nm. In yet another embodiment, improvements may be realized by attenuating light using a filter substantially centered at a wavelength of 620 nm with a full-width at half-maximum of about 55 nm.

Additionally, a filter may attenuate light wavelengths in multiple ranges. For example, an embodiment of a filter may attenuate light at about 620 nm in addition to attenuating light at about 480 nm. In another embodiment, a filter may preferentially attenuate light wavelengths from about 450 nm to about 510 nm and from about 580 nm to about 640 nm. In yet another embodiment, a filter may attenuate light between about 470 and about 490 and between about 610 nm and about 630 nm.

An optical filter may be made in accordance with the previously described processes and using the previously described materials. For example, a 620 nm optical filter may comprise a high pass filter, a low pass filter, or an optical notch filter. The optical notch filter may comprise a plurality of layers of dielectric materials, nanoparticles distributed on or embedded in a host medium, or a combination thereof. In addition, any of the aforementioned combinations may be used in conjunction with a dye incorporated in a substrate. By way of example, producing short pass or notch filters may include using alternating layers of high and low refractive index materials. Example low index dielectric materials include $MgF_2$ and $SiO_2$. Example high index materials include metal oxides such as $TiO_2$, $Ti_3O_5$, $ZrO_2$, and $Ta_2O_5$, and $Si_3N_4$. Numerous other suitable materials can be used, including polymer layers.

Similarly to the embodiments that are intended to attenuate wavelengths absorbed by the melanopsin ganglion cells and were described previously, an optical filter designed to attenuate wavelengths at about 620 nm may be manufactured according to a similar FOM. The light dose D received at about 620 nm can be written $$D_{rec,620} = \int L(\lambda) T(\lambda) R_{620}(\lambda) d\lambda \quad (12)$$

where L is the light spectrum (in terms of intensity, power, photons/sec, etc.), T is the spectral transmission of a filter lying between the light source and the eye, and $R_{620}$ is the idealized response spectrum at about 620 nm, which may be estimated as a Gaussian function centered at 620 nm with a full-width at half-maximum of 50, 55 or 60 nm, although other values are anticipated and may prove therapeutic. For generality, it is assumed that L=1 so as not to limit discussion to any specific light source, however analyses may be performed for any light source of known spectrum.

A similar dose can be calculated in association with the visual response spectrum $$D_{vis} = \int L(\lambda) T(\lambda) V(\lambda) d\lambda \quad (13)$$

where V represents the normalized visual response spectrum.

The effect of an optical filter, such as a nanoparticle notch filter, is to reduce the dose, as described by taking the ratio of dose calculated with the filter to dose without the filter, for example $$N_{rec,620} = \frac{D_{rec,620}}{D_{rec,620}(T=1)}$$

The "attenuation" of the dose may be written as, for example, $$A_{rec,620} = 1 - N_{rec,620} = 1 - \frac{D_{rec,620}}{D_{rec,620}(T=1)}$$

An FOM can also be defined which compares the blocking of the light at about 620 nm to the blocking of the visual response spectrum $$FOM = \frac{1 - \frac{D_{rec,620}}{D_{rec,620}(T=1)}}{1 - \frac{D_{vis}}{D_{vis}(T=1)}} \quad (14)$$

which represents the ratio of the attenuation of light at about 620 nm to the attenuation of light across the visible spectrum, where a value of FOM>1 may be desirable. Using the method described above to estimate the visual response at about 620 nm, the comparison becomes more stringent as a smaller full width half maximum value is used. For example, when $R(\lambda)$, the Gaussian distribution used in the estimate, has a full width half maximum of 50 nm describes a more specific optical filter than that when the estimate includes an $R(\lambda)$ having a 60 nm full width half maximum.

The optical filter may comprise a multilayer dielectric film similar to that described for the attenuation of light to which melanopsin cells are sensitive, or the optical filter may comprise a nanoparticle-based optical filter, a color filter, a tint, a resonant guided-mode filter, a rugate filter, or any combination thereof. A nanoparticle-based optical notch filter may comprise nanoparticles distributed on the surface of or embedded in a host medium. Such a filter may therefore be used in a substantially transparent host medium, such as the lens material of eyeglasses or simply applied to a surface thereof. For example, the filter may be disposed on the surface of eyeglass lenses to attenuate light approaching a user's eyes. In another application, the filter may be disposed on the source of light directly, for example, over an electronic display such as computer screen or on a lighting source such as a light bulb or a window.

The attenuation of light by nanoparticle-based notch filter may be adjusted via the shape of the nanoparticles, the amount or density of nanoparticles on or embedded in the host medium, the composition of the nanoparticles, the size of the nanoparticles, and the index of refraction of the host medium. The attenuation spectrum of a nanoparticle-based optical notch filter may therefore be tuned to a particular curve by selecting materials and distributions that center the curve at a desired wavelength and a produce an attenuation curve with a maximum attenuation at a desired wavelength value and an appropriate shape and full width half maximum.

For example, increasing the index of refraction of the host medium of the nanoparticles may shift the attenuation spectrum toward longer wavelengths, as may utilizing larger particle sizes, including solid and core-shell particles, and/or utilizing other metals. The attenuation spectrum changes because the attenuation is due, at least in part, to localized surface plasmonic resonance (LSPR). The scattering due to the LSPR is proportional to the relative index of the refraction of the host medium. Therefore, when the index of refraction of the host medium increase, not only does the attenuation spectrum redshift, but the amount of scattering, and hence the amount of attenuation of light, increases as well.

The position and amount of scattering due to the LSPR is at least partially dependent on the relative index of refraction between the particles and the host medium. The relative index of refraction can also, therefore, be altered by changing the nanoparticle composition. The nanoparticles may be solid, consisting of a single material, or a core-shell composition having a core of a first material and a shell of a second material. In either case, the materials may be a single element, a compound, or an alloy. As described earlier, the nanoparticles may include metallic nanoparticles (e.g. Al, Ag, Au, Cu, Ni, Pt), dielectric nanoparticles (e.g. $TiO_2$, $Ta_2O_5$, etc.), semiconductor nanoparticles or quantum dots (e.g. Si, GaAs, GaN, CdSe, CdS, etc.), magnetic nanoparticles, core-shell particles consisting of one material in the core and another serving as a shell, other nanoparticles, or combinations thereof. By way of example, increasing the proportion of Ag in an Ag/Al alloy solid nanoparticle may redshift and increase the amplitude of the attenuation curve for that nanoparticle.

In addition, the nanoparticles used may have cross-sections including a circle, an ellipse, a rectangle, a hexagon, an octagon, or other polygon. Spherical particles have the most focused spectrum because they have a single, narrow primary peak that allows for optimization using size and composition changes. However, it is possible to utilize a combination of particles of other shapes in order to develop a desired filter spectrum. One may broaden the extinction spectrum of a 40 nm spherical nanoparticle filter by simply introducing, for example, cubic nanoparticles or octahedral nanoparticles of an equivalent size.

In contrast, the attenuation curve of a core-shell nanoparticle may be tuned by altering the relative thicknesses of the core and shell. By way of example, decreasing the thickness of an Ag shell relative to the size of a $SiO_2$ core may reduce the full width half maximum of the attenuation spectrum. Shapes of these particles may be spherical, ellipsoidal, otherwise shaped, or combinations thereof. The shape of the particles may also affect the shape and amplitude of the attenuation curve. In an embodiment, the optical filter comprises spherical core-shell nanoparticles. In a further embodiment, the spherical core-shell nanoparticles have an Ag shell and a Si core. In a yet further embodiment, the spherical Ag/Si core-shell nanoparticles have an Ag shell with a radial thickness of 45 nm and a Si core with a radius of 15 nm.

Figure 23:
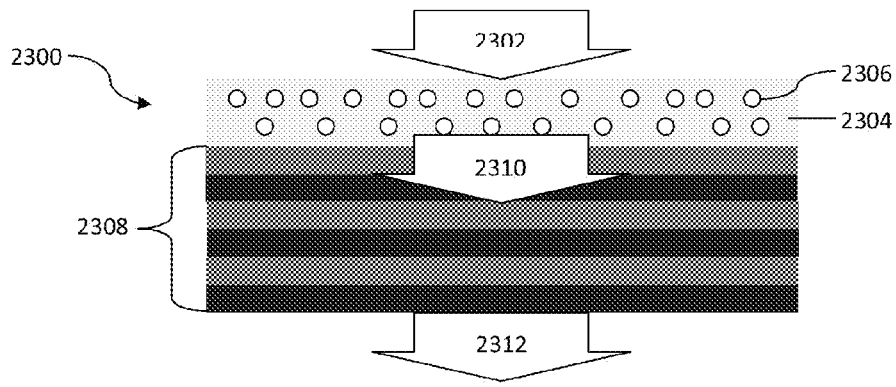
FIG. 23 illustrates an embodiment of a composite filter configured to preferentially attenuate two ranges of wavelengths.

FIG. 23 depicts a nanoparticle-based optical filter used in conjunction with a multilayer thin film filter to form a composite filter 2300. A first filter may attenuate light in a first range of wavelengths, thereby substantially reducing or removing those wavelengths in the light spectrum entering the second filter. In the depicted embodiment, ambient light 2302 may enter a filter comprising nanoparticles 2304 that may be disposed on or embedded in a host medium 2306 that is disposed on a surface of the thin film filter 2308. Alternatively or in addition, a thin film filter and a nanoparticle-based filter may be disposed on opposing surfaces of a substrate, such as the lenses of eyeglasses. In another embodiment, nanoparticles may be embedded within a thin film filter, and one or more layers of the thin film may be the host medium for the nanoparticle-based filter. The ambient light 2302 that enters host medium 2306 with nanoparticles 2304 embedded therein may be sunlight. The attenuated light 2310 that enters the thin film filter 2308 may have a reduced amount of light in the range attenuated by the nanoparticles 2304. The filtered light 2312 that exits the composite filter 2300 may be attenuated in two ranges of wavelengths. Similarly, a "double notch" filter may be implemented entirely through the use of multi-layer thin film coatings.

Figure 24:
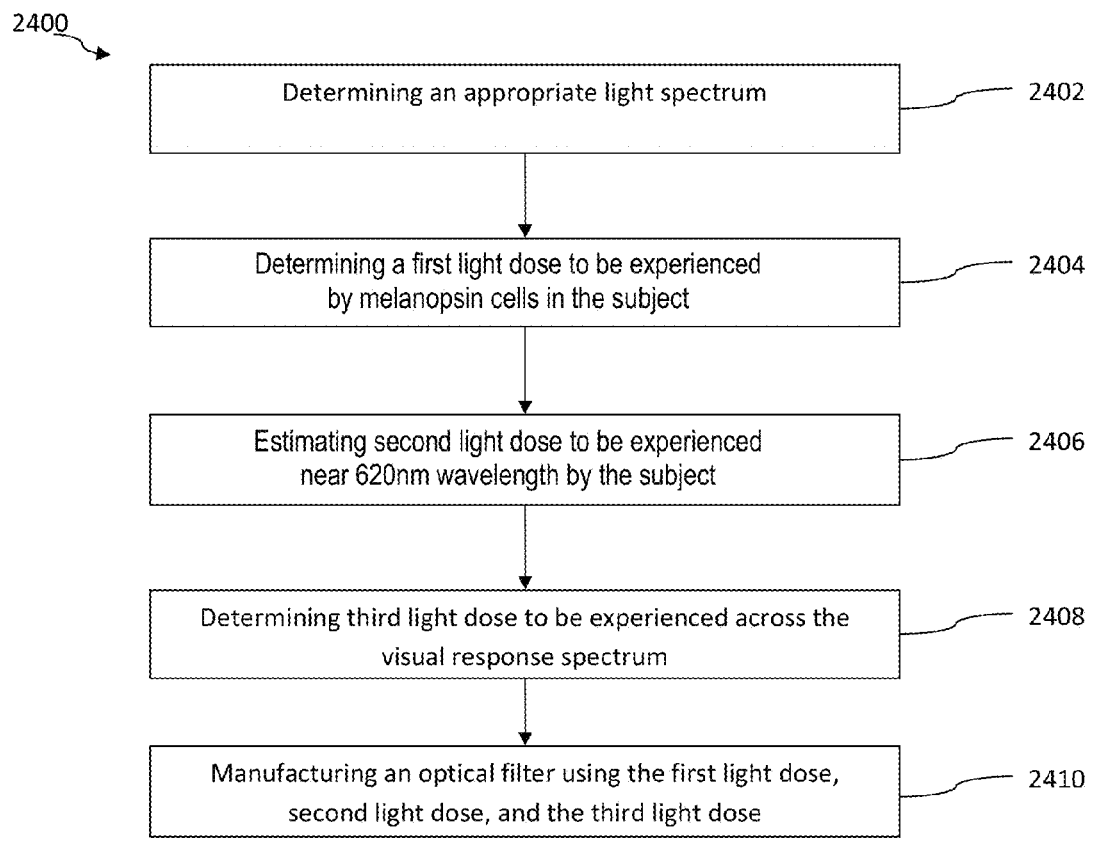
FIG. 24 illustrates an embodiment of a method of manufacturing a composite optical filter.

FIG. 24 illustrates an embodiment of a method 2400 of manufacturing a composite optical filter for reducing the frequency and/or severity of photophobic responses. The method 2400 may be used to design at least one embodiment of a composite filter described herein. The method 2400 may include determining the appropriate light spectrum, as illustrated by act 2402. Determining the appropriate light spectrum may include consideration of specific lighting conditions, such as taking spectrophotometric measurements, in conditions such as indoor fluorescent lighting and/or computer screens in an office, shopping, or home environment, or outdoor lighting such as sunlight experienced due to normal outdoor activities or sporting activities.

A first light dose to be experienced by the subject may be determined (using, for example, Equation 1), as illustrated by act 2404. A second light dose to be experienced by a human eye at a wavelength at about 620 nm may be estimated (using, for example, Equation 12), as illustrated by act 2406. A third light dose to be experienced across the visual response spectrum may be determined (using, for example, Equation 13), as illustrated by act 2408. An optical filter may be designed and manufactured using the first light dose, the second light dose, and the third light dose, as illustrated by act 2410. The first light dose and the second light dose may each be used with the third light dose to determine a figure of merit (FOM) for each as described herein. In other embodiments, the dose across the visual response spectrum may be considered for a portion or portions of the visible spectrum. For example, more or less than the entire visual response spectrum may be used.

Figure 25:
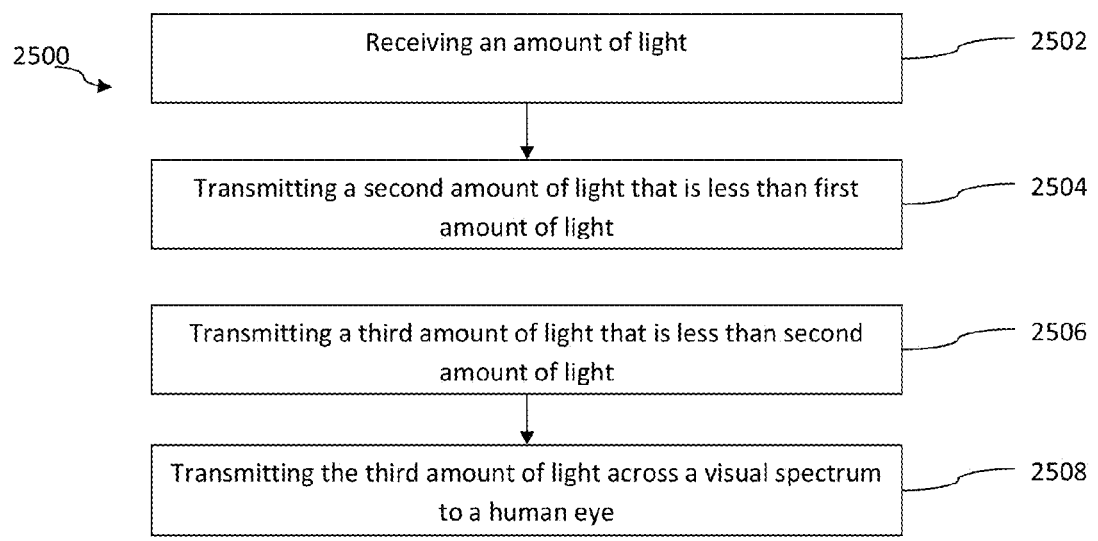
FIG. 25 illustrates an embodiment of a method using a composite filter for reducing the frequency and/or severity of photophobic responses or for modulating circadian cycles.
Figure 26A:
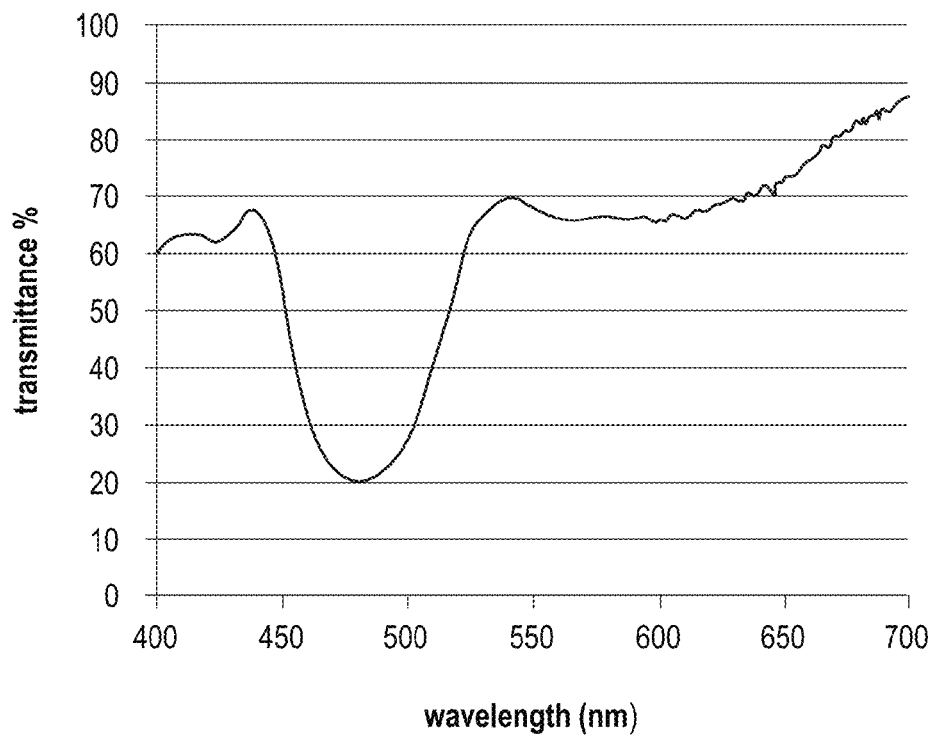
FIGS. 26A and B illustrate the transmission spectra of gray tinted lenses coatings centered at 480 nm and 620 nm, respectively.
Figure 26B:
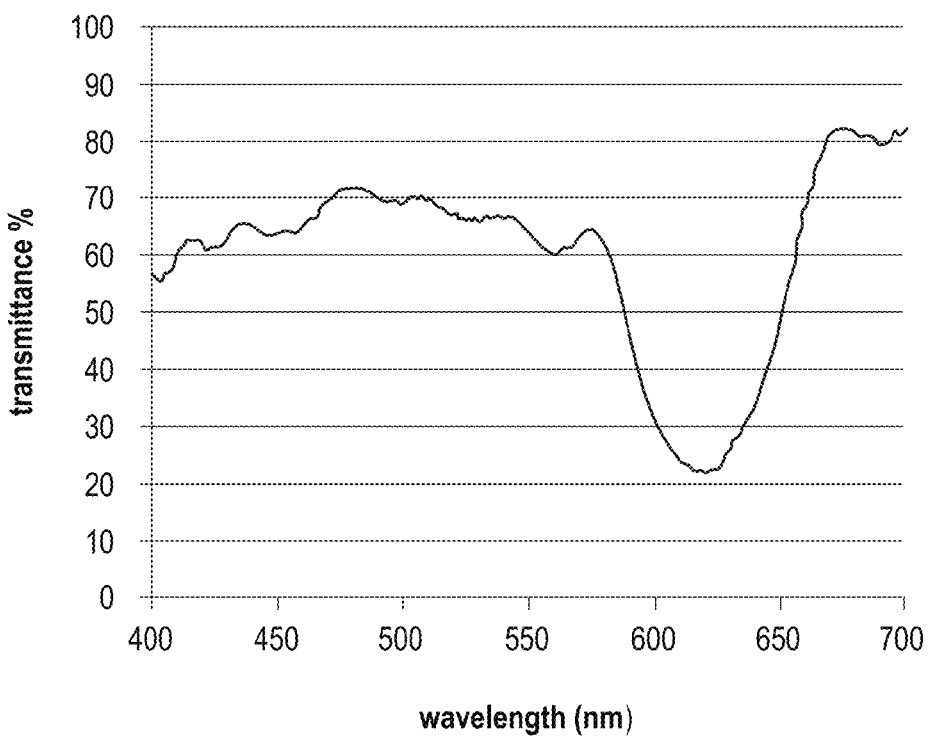

FIG. 25 illustrates an embodiment of a method 2500 using a composite filter for reducing the frequency and/or severity of photophobic responses or for modulating circadian cycles. The method 2500 may be used in conjunction with at least one embodiment of a composite filter described herein. The method 2500 may include receiving an amount of light, as illustrated by act 2502. The light received may include direct or indirect light from one or more light sources. A first amount of light that is attenuated preferentially across the action potential spectrum of the melanopsin cells may be transmitted, as illustrated by act 2504. A second amount of light that is attenuated preferentially in a wavelength range at about 620 nm may be transmitted, as illustrated by act 2506. A third amount of light may then be transmitted to a human eye, as illustrated by act 2508. In other embodiments, the dose across the visual response spectrum may be reduced or separated. For example, more or less than the entire visual response spectrum may be used.

Efficacy testing has been conducted verifying the benefits of attenuating light near about 480 nm and 620 nm. Preliminary testing included a prospective, double-masked, crossover clinical study to determine the efficacy of customized, thin film spectacle coatings in the treatment of chronic migraine. Subjects wore two different spectacles during the trial: one coating was a notch filter at 480 nm. The other coating was a notch filter at 620 nm. Typical transmission spectra of gray tinted lenses with the different coatings used in this study are shown in FIGS. 23A and 23B. The 480 nm notch filter shown blocks about 68% of light absorption by melanopsin, and blocks 42% of visible light. The 620 nm notch filter shown blocks about 66% of light absorption centered at 620 nm with a ~55 nm width and blocks about 42% of visible light. The 480 nm filters used in the study had average blocking around 480 nm of 68±6% and average visible blocking of 44±4%. The 620 nm filters used in the study had average blocking around 620 nm of 67±2% and average visible blocking of 43±4%. Neither the subjects nor the clinical coordinators were informed which lenses had a 480 nm notch filter and which had a 620 nm notch filter. Subjects in the study had to carry a diagnosis of chronic migraine, meaning that they have at least 15 headache-days per month. Individuals with at least 15 headache-days per month are considered the most severely affected migraine patients.

To assess the efficacy of the intervention, the 6-question "Headache Impact Test" ("HIT-6") was chosen as the primary outcome measure. The HIT-6 is a 6-question instrument that has been designed and validated to assess the impact of headaches on a person's life. The score is a continuous variable that ranges from a minimum of 36 to a maximum of 78. A score less than 50 indicates that headaches are having little impact on one's life, a score of 50-55 indicates "some impact," a score of 56-59 indicates "substantial impact," and a score over 60 is consistent with a "very severe impact" of headaches.

Subjects first completed a four-week "pre-wash" during which no study lenses were worn. This period helped establish base-line characteristics of their headaches. Subjects were randomized to wear either one or the other lens first, utilizing block randomization. They were instructed to wear the spectacles full-time for two weeks. They then had a two-week "washout" period during which no study lenses were worn. The subjects then wore the other lens for another two-week period. Finally, subjects underwent a final "post-wash" period during which no study lenses were worn to establish an exit "finish line" for headache characteristics.

There is a considerable amount of variability in the frequency and severity of headaches. In some cases, this variability may occur even in the same patient. The "pre-wash" and "post-wash" periods were added to due to the variability. These additional periods, during which no study lenses are worn, minimized the effect of "baseline drift" in the study subjects.

The HIT-6 questionnaire was administered before the study and after each of the period of the study, resulting in six completed questionnaires for each subject. The study included forty-eight participants initially, and thirty-seven of the participants completed the course of the study. Of the thirty-seven subjects who completed the study, the baseline HIT-6 score was 64.5. Thirty-three of the thirty-seven subjects (89%) had baseline HIT-6 scores greater than or equal to 60. According to the HIT-6 interpretation, these thirty-three subjects have headaches that are having a "very severe impact" on their lives. Both the 480 nm and 620 nm filter lenses displayed a statistically significant reduction in HIT-6 values.

Of the thirty-seven participants that completed the study, nine subjects were able to move out of the "very severe impact" HIT-6 category while wearing the 480 nm lenses; five subjects were able to move out of this category wearing the 620 nm lenses and five subjects were able to move out of this category wearing either of the lenses. Ten subjects experienced at least a 6-point improvement in HIT-6 when wearing the 480 nm lenses, ten subjects experienced at least a 6-point improvement in HIT-6 when wearing the 620 nm lenses and three subjects experienced at least a 6-point improvement in HIT-6 when wearing either of the lenses. This analysis indicates that wearing either the 480 nm or 620 nm spectacle lenses resulted in statistically significant reductions in HIT-6. However, there was no significant difference comparing the effect of the 480 nm lenses to the 620 nm lenses (p=0.195) . . . .

Secondary outcomes gleaned from the diaries, including percent days with severe headache, percent days where activity had to be changed or subject had to go to bed, and percent days requiring an abortive medication, behaved similar to the primary outcome for either the 480 nm or 620 nm spectacle lenses: Subjects experienced significant reductions in these parameters wearing either the 480 nm or 620 nm lenses. There was no significant difference comparing the effect of the 480 nm lenses to the 620 nm lens for any of these three outcomes.

Figure 27:
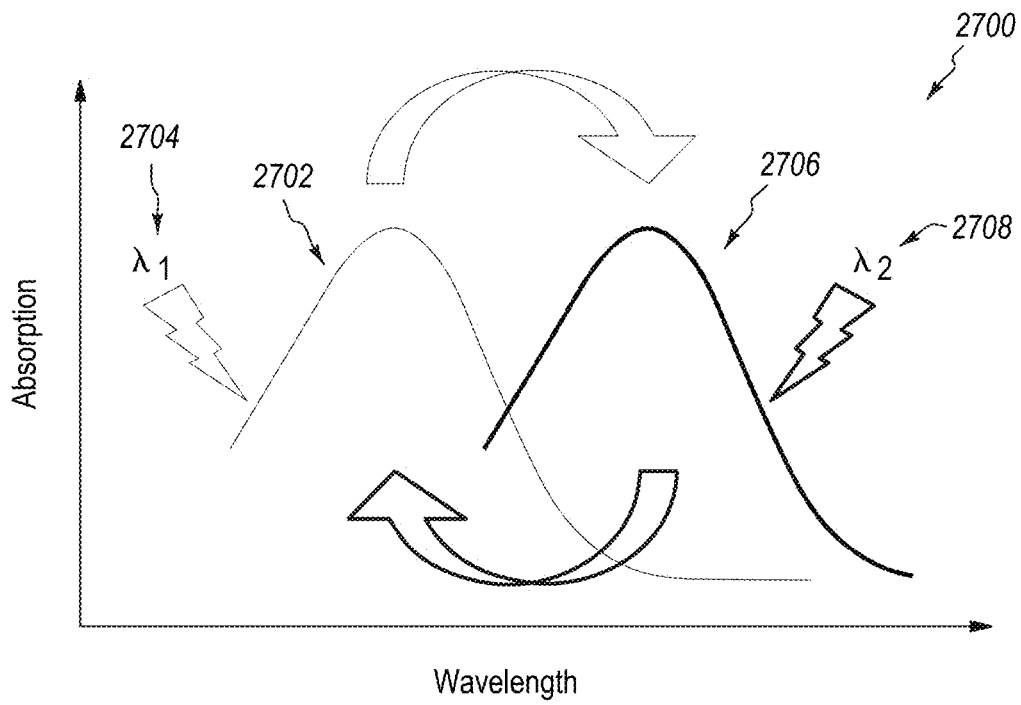
FIG. 27 schematically illustrates the cyclic isomerization of a bistable pigment.

The melanopsin of the melanopsin ganglion cells is a bistable pigment. Melanopsin may undergo an isomerization during exposure to light at certain wavelengths. FIG. 27 is a graph 2700 schematically depicting the cyclic isomerization of a bistable pigment as the pigment is exposed to different wavelengths of light. The bistable pigment may have first isoform that exhibits a first absorption spectrum 2702. The first absorption spectrum absorbs a first wavelength 2704. The first isoform of the bistable pigment may react with the first wavelength 2704. The first wavelength 2704 may isomerize the bistable pigment and may trigger a phototransduction cascade in an associated cell or membrane. In an embodiment, the bistable pigment may be melanopsin and exposure to a first wavelength 2704 may trigger a phototransduction cascade in the melanopsin ganglion cell. Exposure to the first wavelength may cause the bistable pigment to isomerize from the first isoform to a second isoform. The first isoform may be an active 11-cis isoform of melanopsin. The second isoform may be an inactive metamelanopsin isoform. The isomerization of the active 11-cis isoform may lead to the phototransduction cascade.

The second isoform may exhibit a second absorption spectrum 2706. The second absorption spectrum 2706 may absorb a second wavelength 2708. The second isoform of the bistable pigment may react with the second wavelength 2708. In an embodiment, the first isoform may be an active isoform of the bistable pigment and the second isoform may be an inactive isoform of the bistable pigment. In another embodiment, the first isoform may be an inactive isoform of the bistable pigment and the second isoform may be an active isoform of the bistable pigment. In yet another embodiment, the first isoform may be an active isoform of melanopsin and the second isoform may be an inactive isoform of melanopsin.

Figure 28:
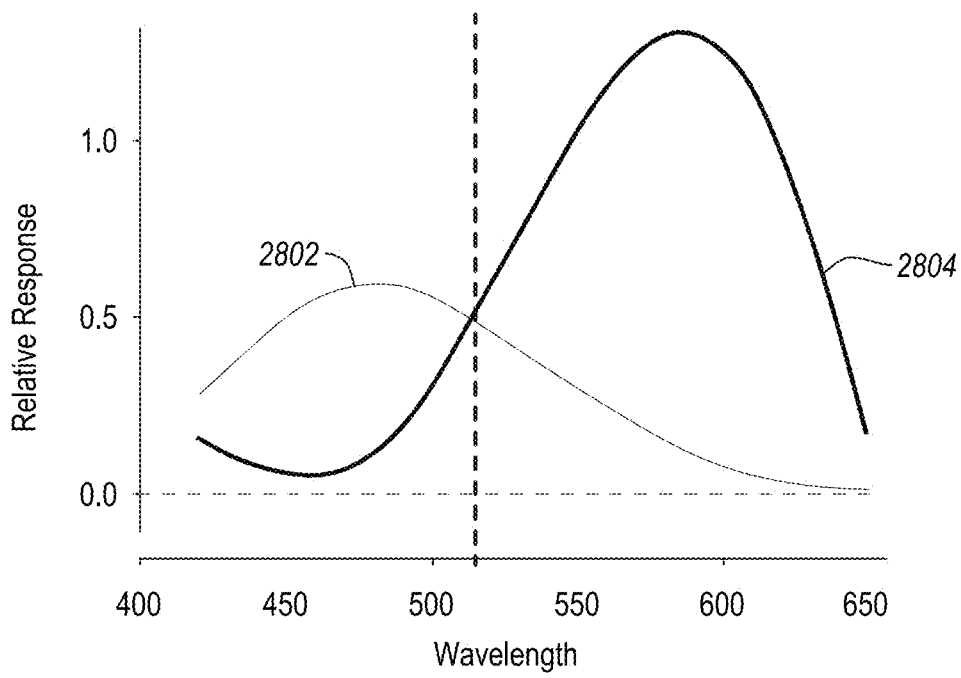
FIG. 28 illustrates the reactive spectra of active and inactive melanopsin in the eye.

FIG. 28 depicts a graph 2800 of an active absorption spectrum 2802 and an inactive absorption spectrum 2804 for melanopsin. The active absorption spectrum 2802 and inactive absorption spectrum 2804 each correspond to an active isoform of melanopsin and an inactive isoform of melanopsin, respectively. "Active" and "inactive" should be understood as referring to the physiological activity of the pigment and the pigment's ability to contribute to photophobic responses in an individual rather than the pigment's ability to absorb light. The active absorption spectrum 2802 may have a maximum at approximately 484 nm. The inactive absorption spectrum 2804 may have a maximum at approximately 587 nm.

The inactive isoform of melanopsin may absorb wavelengths of light according to the inactive absorption spectrum 2804. The light absorbed by the inactive isoform of melanopsin may contribute to the conversion of the inactive isoform to the active form of melanopsin. The active form of melanopsin may contribute to a photophobic response of an individual. In at least one embodiment, an attenuation of light absorbed by the inactive isoform may disrupt the isomerization of melanopsin and reduce symptoms of light sensitivity in some people, such as pain or discomfort in response to light, and the frequency and/or severity of migraine and other headaches, and may also prove effective for some in the treatment of blepharospasm, post-concussion/TBI syndrome, sleep disorders, epilepsy.

In addition to regulating the exposure of melanopsin ganglion cells to light near 480 nm and/or 620 nm, the attenuation of light at the absorption maximum of the inactive absorption spectrum for the inactive isoform of melanopsin may also yield improvements in alleviating symptoms associated with light sensitivity. For example, an optical filter centered at a wavelength of about 590 nm may attenuate the light absorbed by the inactive isoform of melanopsin.

In one embodiment, improvements may be realized by attenuating light between about 560 nm and about 620 nm. In another embodiment, improvements may be realized by attenuating light between about 570 nm and about 610 nm. In yet another embodiment, improvements may be realized by attenuating light using a filter substantially centered at a wavelength of 590 nm with a full-width at half-maximum of about 50 nm.

Additionally, a filter may attenuate light wavelengths in multiple ranges. For example, an embodiment of a filter may attenuate light absorbed by the inactive isoform of melanopsin and light absorbed by the active isoform of melanopsin. In an embodiment, a filter may attenuate light at about 590 nm in addition to attenuating light at about 480 nm. In another embodiment, a filter may preferentially attenuate light wavelengths from about 450 nm to about 510 nm and from about 560 nm to about 620 nm. In yet another embodiment, a filter may attenuate light between about 470 and about 490 and between about 580 nm and about 600 nm.

Similarly to the previously described 480 nm filter and the 620 nm filter, an optical filter capable of attenuating 590 nm light may comprise a high pass filter, a low pass filter, an optical notch filter, or combinations thereof. The optical notch filter may comprise a plurality of layers of dielectric materials, nanoparticles distributed on or embedded in a host medium, or a combination thereof. In addition, any of the aforementioned combinations may be used in conjunction with a dye incorporated in a substrate. By way of example, producing short pass or notch filters may include using alternating layers of high and low refractive index materials. Example low index dielectric materials include $MgF_2$ and $SiO_2$. Example high index materials include metal oxides such as $TiO_2$, $Ti_3O_5$, $ZrO_2$, and $Ta_2O_5$, and $Si_3N_4$. Numerous other suitable materials can be used, including polymer layers.

Similarly to the embodiments that are intended to attenuate wavelengths absorbed by the active isoform of melanopsin and were described previously, an optical filter designed to attenuate wavelengths at about 590 nm may be manufactured according to a similar FOM. The light dose D received at about 590 nm can be written $$D_{rec,590} = \int L(\lambda)T(\lambda)R_{590}(\lambda)d\lambda \quad (15)$$

where L is the light spectrum (in terms of intensity, power, photons/sec, etc.), T is the spectral transmission of a filter lying between the light source and the eye, and $R_{590}$ is the idealized response spectrum at about 590 nm, which may be estimated as a Gaussian function centered at 590 nm with a full-width at half-maximum of 50, 55, or 60 nm, although other values are anticipated and may prove therapeutic. For generality, it is assumed that L=1 so as not to limit discussion to any specific light source, however analyses may be performed for any light source of known spectrum.

A similar dose can be calculated in association with the visual response spectrum $$D_{vis} = \int L(\lambda)T(\lambda)V(\lambda)d\lambda \quad (16)$$

where V represents the normalized visual response spectrum.

The effect of an optical filter, such as a nanoparticle notch filter, is to reduce the dose, as described by taking the ratio of dose calculated with the filter to dose without the filter, for example $$N_{rec,590} = \frac{D_{rec,590}}{D_{rec,590}(T=1)}$$

The "attenuation" of the dose may be written as, for example, $$A_{rec,590} = 1 - N_{rec,590} = 1 - \frac{D_{rec,590}}{D_{rec,590}(T=1)}$$

An FOM can also be defined which compares the blocking of the light at about 590 nm to the blocking of the visual response spectrum $$FOM = \frac{1 - \frac{D_{rec,590}}{D_{rec,590}(T=1)}}{1 - \frac{D_{vis}}{D_{vis}(T=1)}} \quad (17)$$

which represents the ratio of the attenuation of light at about 590 nm to the attenuation of light across the visible spectrum, where a value of FOM>1 may be desirable. Using the method described above to estimate the visual response at about 590 nm, the comparison becomes more stringent as a smaller full width half maximum value is used. For example, when $R(\lambda)$, the Gaussian distribution used in the estimate, has a full width half maximum of 50 nm describes a more specific optical filter than that when the estimate includes an $R(\lambda)$ having a 60 nm full width half maximum.

Figure 29:
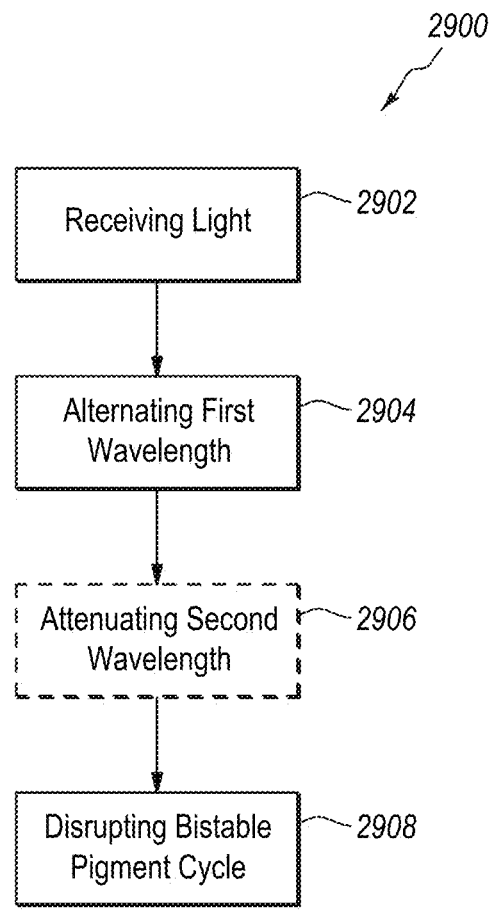
FIG. 29 illustrates an embodiment of a method of disrupting the isomerization of one or both of the bistable isoforms of melanopsin.

FIG. 29 depicts a method 2900 for reducing symptoms associated with photophobic responses. The method 2900 includes receiving 2902 light and attenuating a first wavelength 2904 and, optionally, a second wavelength 2906. The attenuation of the first wavelength may then disrupt the bistable pigment cycle 2908 described in relation to FIG. 27. In an embodiment, the first wavelength may be determined by a maximum of an active absorption spectrum or an inactive absorption spectrum of a bistable pigment. In another embodiment, the first wavelength may be determined by the maximum of the active absorption spectrum 2802 of melanopsin or maximum of the inactive absorption spectrum 2804 described in relation to FIG. 28. In yet another embodiment, the first wavelength may be 480 nm. In a further embodiment, the first wavelength may be 590 nm.

Attenuating a wavelength should be understood to mean preferentially attenuating the wavelength or a range including the wavelength as compared to other portions of the visible spectrum. For example, attenuating a 590 nm wavelength may include transmitting less light at or about the 590 nm wavelength than other light in the visible spectrum. In another example, attenuating a 590 nm wavelength may include blocking substantially all light at or about the 590 nm wavelength and transmitting other light in the visible spectrum.

Attenuating the second wavelength 2906 may include attenuating a portion of a second wavelength different from the first wavelength attenuated. In an embodiment, the second wavelength may be determined by a maximum of an active absorption spectrum or an inactive absorption spectrum of a bistable pigment. In another embodiment, the first wavelength may be determined by the maximum of the active absorption spectrum 2802 of melanopsin or maximum of the inactive absorption spectrum 2804 of melanopsin described in relation to FIG. 28. In yet another embodiment, the first wavelength may be 480 nm. In a further embodiment, the first wavelength may be 590 nm.

Attenuating a first wavelength 2904 and, optionally, attenuating a second wavelength 2906 may disrupt a bistable pigment cycle. Attenuating a first wavelength 2904 may inhibit the isomerization of the bistable pigment from a first isoform to a second isoform. The first isoform may be an active isoform or an inactive isoform. Attenuating a second wavelength 2906 may inhibit the isomerization of the bistable pigment from the second isoform back to the first isoform.

An optical filter capable of attenuating light at or about a 590 nm wavelength may be manufactured and/or tuned by any of the aforementioned processes such that a low pass filter, a high pass filter, or an optical notch filter preferentially attenuates 590 nm light. The filter may include dielectric multi-layers, embedded nanoparticle coatings, a color filter, tint, resonant guided-mode filter, a rugate filter, and any combination thereof. The filter may also include embedded nanoparticle coatings such as metallic nanoparticles, dielectric nanoparticles, semiconductor nanoparticles, quantum dots, magnetic nanoparticles, or core-shell particles having a core material in a core and a shell material serving as a shell.

The terms "approximately," "about," "near," and "substantially" as used herein represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of a stated amount.

It should be noted that, while the invention has been described in connection with the above described embodiments, these descriptions are not intended to limit the scope of the invention to the particular forms set forth, but on the contrary, these descriptions are intended to cover such alternatives, modifications, and equivalents as may be included within the scope of the invention. Any elements of the above-described embodiments may be combined with any other elements of the above-described embodiments. For example, any of the above-described methods of manufacture or methods of light attenuation may be combined with the described optical filters and associated wavelengths. Accordingly, the scope of the present invention fully encompasses other embodiments that may become obvious to those skilled in the art and the scope of the present invention is limited only by the appended claims.

What is claimed is:

1. An apparatus for reducing the frequency and/or severity of photophobic responses or for modulating circadian cycles by controlling exposure of cells in a retina relative to a visible spectrum range of 400 nm to 700 nm, the apparatus comprising:

an optical filter configured to transmit:
light averaged across a first range of wavelengths between about 565 nm and about 615 nm, wherein the transmitted light across the first wavelength range is a dose of light experienced by receptive cells of a subject ($D_{rec,590}$), and
light averaged across a second range of wavelengths within a visible spectrum less than about 565 nm and greater than about 615 nm, wherein the transmitted across the second wavelength range is a dose of light experienced over the visual spectrum
wherein the optical filter has a figure of merit (FOM) defined by:

$$FOM = \frac{1 - \frac{D_{rec,590}}{D_{rec,590}(T=1)}}{1 - \frac{D_{vis}}{D_{vis}(T=1)}}$$

where $D_{rec,590}$ (T=1) is the light across the first wavelength range in the absence of an optical filter, and $D_{vis}$ (T=1) is the light across the second wavelength range in the absence of an optical filter, wherein the figure of merit of said optical filter is at least 1.3.

2. The apparatus of claim 1, wherein said light across the first wavelength range is approximately all of the light between about 565 nm and about 615 nm wavelengths and wherein said light across the second wavelength range is approximately all of the light outside of the first wavelength range.

3. The apparatus of claim 1, wherein said light across the first wavelength range is substantially all light above a short-pass filter wavelength between about 565 nm and 615 nm and said light across the second wavelength range is all light across the visual spectrum with a wavelength below said short-pass filter wavelength.

4. The apparatus of claim 1, wherein the optical filter is configured to transmit about 45% of the light across the first wavelength range and about 60% of the light across the second wavelength range.

5. The apparatus of claim 1, wherein the figure of merit of said optical filter is greater than 1.3, is greater than about 1.5, is greater than about 1.8, is greater than about 2.75, is greater than about 3, or is greater than about 3.3.

6. The apparatus of claim 1, wherein the optical filter includes dielectric multi-layers, embedded nanoparticle coatings, a color filter, tint, resonant guided-mode filter, a rugate filter, or any combination thereof.

7. The apparatus of claim 6, wherein the embedded nanoparticle coatings include at least one of metallic nanoparticles, dielectric nanoparticles, semiconductor nanoparticles, quantum dots, magnetic nanoparticles, or core-shell particles having a core material in a core and a shell material serving as a shell.

8. The apparatus of claim 7, wherein the metallic nanoparticles include at least one of Al, Ag, Au, Cu, Ni, or Pt, wherein the dielectric nanoparticles include at least one of $TiO_2$ or $Ta_2O_5$.

9. The apparatus of claim 7, wherein the semiconductor nanoparticles or quantum dots include at least one of Si, GaAs, GaN, CdSe, or CdS.

10. The apparatus of claim 7, wherein a shape of embedded nanoparticles in the embedded nanoparticle coatings is spherical or elliptical.

11. An apparatus for reducing the frequency and/or severity of photophobic responses by controlling light exposure to melanopsin ganglion cells in a retina, the apparatus comprising:
a composite optical filter configured to transmit:
light averaged across a Gaussian function with a central wavelength of about 590 nm and a full-width at half-maximum of about 50 nm, the transmitted light across the Gaussian function with a central wavelength of about 590 nm is a dose of light experienced by the melanopsin ganglion cells of a subject ($D_{rec,590}$); and
light averaged across a Gaussian function with a central wavelength of about 550 nm and a full-width at half-maximum of about 134 nm, the transmitted light across the Gaussian function with a central wavelength of about 550 nm is a dose of light experienced over the visual response spectrum ($D_{vis}$); and
wherein a ratio including the light averaged across the Gaussian function with a central wavelength of about 590 nm and the light averaged across the Gaussian function with a central wavelength of about 550 nm is defined as a figure of merit (FOM) of the optical filter, the figure of merit being determined by:

$$FOM = \frac{1 - \frac{D_{rec,590}}{D_{rec,590}(T=1)}}{1 - \frac{D_{vis}}{D_{vis}(T=1)}}$$

where $D_{rec,590}$ (T=1) is the light across the Gaussian function with a central wavelength of about 590 nm in the absence of an optical filter, and $D_{vis}$ (T=1) is the light across the across the Gaussian function with a central wavelength of about 550 nm in the absence of an optical filter, wherein the figure of merit of said optical filter is at least 1.3.

12. The apparatus of claim 11, wherein the optical filter includes at least one of a dielectric multi-layer coating, embedded nanoparticle coating, a color filter, tint, resonant guided-mode filter, a rugate filter, or any combination thereof.

13. The apparatus of claim 12, wherein the embedded nanoparticle coating includes at least one of metallic nanoparticles, dielectric nanoparticles, semiconductor nanoparticles, quantum dots, magnetic nanoparticles, or core-shell particles having a core material in a core and a shell material serving as a shell.

14. The apparatus of claim 13, wherein the metallic nanoparticles include at least one of Al, Ag, Au, Cu, Ni, Pt, or other metallic nanoparticles, wherein the dielectric nanoparticles include at least one of $TiO_2$, $Ta_2O_5$, or other dielectric nanoparticles.

15. An apparatus for reducing the frequency and/or severity of photophobic responses or for modulating circadian cycles by controlling exposure of cells in a retina, relative to a visible spectrum range of 400 nm to 700 nm, the apparatus comprising: an optical filter configured to transmit:
light averaged across a first wavelength range of between about 565 nm and about 615 nm, wherein the transmitted light across the first wavelength range is a dose of light experienced by receptive cells of a subject ($D_{rec,590}$),
light averaged across a second wavelength range of between about 454 nm and about 506 nm, wherein the transmitted light across the second wavelength range is a dose of light experienced by receptive cells of a subject ($D_{melan}$),
light averaged across a third wavelength range within a visible spectrum less than about 454 nm, between about 506 nm and about 565 nm, and greater than about 615 nm, the transmitted light across the third wavelength range is a dose of light experienced over the visual spectrum ($D_{vis}$), and
wherein a ratio including the light across the first wavelength range and the light across the third wavelength range is defined as a figure of merit (FOM) of the optical filter, the figure of merit being determined by:

$$FOM = \frac{1 - \frac{D_{rec,590}}{D_{rec,590}(T=1)}}{1 - \frac{D_{vis}}{D_{vis}(T=1)}}$$

where $D_{rec,590}$ (T=1) is the light across the first wavelength range in the absence of an optical filter, and $D_{vis}$ (T=1) is the light across the third wavelength range in the absence of an optical filter, wherein the figure of merit is at least 1.3, and
wherein a ratio including the light across the second wavelength range and the light across the third wavelength range is defined as a figure of merit (FOM) of the optical filter, the figure of merit being determined by:

$$FOM = \frac{1 - \frac{D_{melan}}{D_{melan}(T=1)}}{1 - \frac{D_{vis}}{D_{vis}(T=1)}}$$

where $D_{melan}$ (T=1) is the light across the second wavelength range in the absence of an optical filter, and $D_{vis}$ (T=1) is the light across the third wavelength range in the absence of an optical filter, wherein the figure of merit is at least 1.3.

16. An apparatus for reducing the frequency and/or severity of photophobic responses by controlling light exposure to melanopsin ganglion cells in a retina, relative to a visible spectrum range of 400 nm to 700 nm, the apparatus comprising: an optical filter configured with:
a light transmission fraction, averaged across wavelengths between about 565 nm and about 615 nm, less than an amount $T_{rec,590}$, wherein $T_{rec,590}$ is a light across a first wavelength range in the absence of an optical filter and
a light transmission fraction, averaged across wavelengths within a visible spectrum less than about 565 nm and greater than about 615 nm, greater than an amount $T_{vis}$, wherein $T_{vis}$ is the light across a second wavelength range in the absence of an optical filter, and
wherein a ratio including said light transmission fractions is defined as a figure of merit (FOM) of the optical filter, the figure of merit being determined by:

$$FOM = \frac{1 - T_{rec,590}}{1 - T_{vis}}$$

wherein the figure of merit of said optical filter is at least 1.6.

17. An apparatus for reducing the frequency and/or severity of photophobic responses by controlling light exposure to melanopsin ganglion cells in a retina, relative to a visible spectrum range of 400 nm to 700 nm, the apparatus comprising: an optical filter configured with:
 a light transmission fraction, averaged across wavelengths between about 454 nm and about 506 nm, less than an amount $T_{melan}$, wherein $T_{melan}$ is a light across a first wavelength range in the absence of an optical filter and
 a light transmission fraction, averaged across wavelengths within a visible spectrum less than about 454 nm and greater than about 506 nm, greater than an amount $T_{vis}$, wherein $T_{vis}$ is the light across a second wavelength range in the absence of an optical filter,
 wherein a ratio including said light transmission fractions is defined as a figure of merit (FOM) of the optical filter, the figure of merit being determined by:

$$FOM = \frac{1 - T_{melan}}{1 - T_{vis}}$$

wherein the figure of merit of said optical filter is at least 1.6.

* * * * *